United States Patent [19]

Lindenbaum

[11] Patent Number: 5,591,709
[45] Date of Patent: *Jan. 7, 1997

[54] COMPOSITIONS AND METHODS FOR TREATING WOUNDS

[75] Inventor: Ella Lindenbaum, Haifa, Israel

[73] Assignee: Life Medical Sciences, Inc., Princeton, N.J.

[*] Notice: The term of this patent shall not extend beyond the expiration date of Pat. No. 5,461,030.

[21] Appl. No.: 374,944

[22] Filed: Jan. 18, 1995

Related U.S. Application Data

[63] Continuation-in-part of Ser. No. 25,216, Mar. 2, 1993, abandoned, Ser. No. 937,486, Aug. 28, 1992, abandoned, and Ser. No. 158,808, Nov. 29, 1993, Pat. No. 5,461,030, which is a continuation of Ser. No. 752,849, Aug. 30, 1991, abandoned, said Ser. No. 25,216, is a continuation-in-part of Ser. No. 937,486, which is a continuation-in-part of Ser. No. 752,849.

[51] Int. Cl.⁶ .......................... A61K 9/06; A61K 31/195; A61K 38/27; A61K 38/28

[52] U.S. Cl. .............. 514/4; 424/484; 424/486; 424/487; 424/488; 514/3; 514/12; 514/21; 514/567

[58] Field of Search .................... 424/484, 485, 424/486, 487, 488; 435/240.31; 514/3, 4, 12, 21, 567; 530/350, 399

[56] References Cited

U.S. PATENT DOCUMENTS

| | | | |
|---|---|---|---|
| 3,664,925 | 5/1972 | Sonenberg et al. | 435/68.1 |
| 3,904,753 | 9/1975 | Sonenberg et al. | 514/21 |
| 4,056,520 | 11/1977 | Sonenberg et al. | 530/324 |
| 4,444,760 | 4/1984 | Thomas, Jr. | 514/21 |
| 4,503,037 | 3/1985 | Szijjarto et al. | 424/94.4 |
| 4,658,021 | 4/1987 | Goeddel et al. | 530/399 |
| 4,673,649 | 6/1987 | Boyce et al. | 435/240.25 |
| 4,696,917 | 9/1987 | Lindstrom et al. | 514/54 |
| 4,713,375 | 12/1987 | Lindstrom et al. | 514/57 |
| 4,837,379 | 6/1989 | Weinberg | 514/2 |
| 4,863,899 | 9/1989 | Todaro | 514/9 |
| 4,886,786 | 12/1989 | Lindstrom et al. | 514/54 |
| 4,940,666 | 7/1990 | Boyce et al. | 435/240.2 |
| 5,013,714 | 5/1991 | Lindstrom et al. | 514/7 |
| 5,034,375 | 7/1991 | Antoniades et al. | 514/12 |
| 5,035,887 | 7/1991 | Antoniades et al. | 424/85.2 |
| 5,051,443 | 9/1991 | Neufeld et al. | 514/420 |
| 5,124,392 | 6/1992 | Robertson et al. | 424/427 |
| 5,165,938 | 11/1992 | Knighton | 514/2 |
| 5,204,325 | 4/1993 | Lindstrom et al. | 514/4 |
| 5,218,093 | 6/1993 | Gao et al. | 530/399 |
| 5,219,739 | 6/1993 | Tischer et al. | 435/69.4 |
| 5,336,614 | 8/1994 | Brown et al. | 435/240.31 |

FOREIGN PATENT DOCUMENTS

| | | |
|---|---|---|
| 308238 | 3/1989 | European Pat. Off. |
| 0364266 | 4/1990 | European Pat. Off. |
| 0516901 | 12/1992 | European Pat. Off. |
| M7800 | 5/1970 | France |
| 9003810 | 4/1990 | WIPO |
| 9304691 | 3/1993 | WIPO |

OTHER PUBLICATIONS

Tsao et al., "Clonal Growth of Normal Human Epidermal Keratinocytes in a Defined Medium," *J. of Cellular Physiology*, 110, 219, 1982.

Wille et al., "Integrated Control of Growth and Differentiation of Normal Human . . ." *J. of Cellular Physiology*, 121, 31, 1984.

Hayward et al., "Animal Models of Wound Contraction," *Clinical and Experimental Approaches to Dermal . . .*, 301–312, 1991, Wiley–Liss, Inc.

Mulder, "If Wounds Could Talk," *Clinical and Experimental Approaches to Dermal and Epidermal Repair:Normal and Chronic Wounds*, 55–66, 1991, Wiley–Liss, Inc.

Ham, "Growth of Normal Human Cells in Defined Media," 16–30 (not dated).

Liss, *Culture of Animal Cells*, 238–241, 1988, Alan R. Liss, Inc., New York.

Barnes et al., "Serum–Free Cell Structure: A Unifying Approach," *Cell*, v. 22, 649, 1980.

Boyce et al., "Calcium–Regulated Differentiation of Normal Human Epidermal Keratinocytes . . ." *J. of Investigative Dermatology*, 81, 335, 1983.

Lynch et al., *Proc. Natl. Acad. Sci.*, 84, 7696–7700, Nov. 1987.

European Search Report (Dec. 20, 1994) for Appl. Ser. No. 92919722.6.

Diane Krasner, ed. *Chronic Wound Care: A Clinical Source Book for Healthcare Professionals*, pp. 311–317 (no date).

Adams, Cell Culture for Biochemists, publ. 1980 by Elsevier/North–Holland Biomedical Press (Amsterdam), pp. 84–89, 251, 252.

Maciag et al., "An Endocrine Approach to the Control of Epidermal Growth," *Science*, v. 211, Mar. 27, 1981, pp. 1452–1454.

Herndon et al., "Increased Rates of Wound Healing in Burned Guinea Pigs . . ." *Surgical Forum*, v. XXX, 1979, pp. 95–97.

Pick et al, "Effect of Analogues of Steroid and Thyroxine Hormones . . ." *J. Periodontal Research*, v. 9, 1974, pp. 290–297.

Pierce et al. "Platelet–derived Growth Factor and Transforming Growth Factor . . ." *J. Cell Bio.*, Jul. 1989.

*Primary Examiner*—Jeffrey E. Russel
*Attorney, Agent, or Firm*—Henry D. Coleman; R. Neil Sudol

[57] ABSTRACT

The present invention relates to wound treatment formulations and methods for treating wounds utilizing these formulations. The formulations according to the present invention are useful for treating wounds by accelerating wound healing. These formulations generally comprise an effective amount of a non-steroidal anabolic hormone such as insulin, growth hormone, triiodothyronine, thyroxine or mixtures thereof, in combination with a cellular nutrient medium, preferably MCDB 153.

38 Claims, 15 Drawing Sheets

COMPOSITIONS AND METHODS FOR TREATING WOUNDS

This application is a continuation-in-part application of U.S. patent application Ser. No. 08/025,216, filed Mar. 2, 1993, now abandoned which is a continuation-in-part application of Ser. No. 937,486, filed Aug. 28, 1992, now abandoned, which is a continuation-in-part of U.S. patent application Ser. No. 752,849, filed Aug. 30, 1991, now abandoned, and a continuation-in-part of applications Ser. No. 937,486, filed Aug. 28, 1992, now abandoned.

FIELD OF THE INVENTION

The present invention relates to novel compositions and methods using such compositions for promoting wound healing of skin and related tissues. More particularly, the invention relates to wound healing compositions which are based on a cellular nutrient medium, generally at least a minimum essential medium, in combination with at least one non-steroidal anabolic hormone, preferably three anabolic hormones.

BACKGROUND OF THE INVENTION

A skin wound is defined as a breach in the continuity of any body tissue caused by a minimal direct injury to the skin. There are many instances where a quick closure of the wounded skin will promote a beneficial response. Generally, quick closure of wounded skin can be achieved either by conservative methods such as the application of medicaments, or alternatively, by using various surgical procedures including suturing, split skin grafting or grafting of new skin grown in culture.

The closure of a wound with skin cells is performed using two methods: either by grafting skin grown in culture or alternatively, by split skin grafting. These two methods are applicable, however, only after a suitable base of granulation tissue has first developed in the wound, the development of which may be quite prolonged or complicated. Split skin grafting, although more common, requires compositions which contain materials for maintaining organ viability and treatment of the wounds for the repair of injury to the skin.

Among the most common injuries to skin are burns. Burn causes destruction of the epidermis and deeper cutaneous and subcutaneous tissues, most of which can be regenerated by the normal healing response if the area burned is not extensive or contaminated. Burns cause more than 2,000,000 injuries annually in the U.S.A., and more than 10,000 deaths each year result from serious burn injuries.

S. T. Boyce et al., in *The Journal of Investigative Dermatology*, 81: 33S–40S, 1983) describes compositions based upon a serum-free culture system to culture normal human epidermal keratinocytes. These compositions comprise optimized nutrient medium MCDB 153 supplemented with epidermal growth factor, insulin, hydrocortisone, ethanolamine, phospho-ethanolamine and whole Bovine Pituitary Extract (wBPE). It is mentioned that the wBPE initiates the primary culture and that cellular senescence occurs after about forty population doublings. It has also been reported in the *Journal of Cellular Physiology*, 110, 219, (1982), that the incorporation of Fetal Bovine Serum Protein (FBSP) may replace whole serum for culturing human epidermal keratinocytes and that the presence of F12 would eliminate the need for wBPE. As presently known, wBPE is not a common reagent which can be easily reproducibly prepared, its constitution not being constant.

J. J. Wille, Jr. et al., in the *Journal of Cellular Physiology*, 121, 31, (1984) describes the effects of growth factors, hormones and calcium on the growth and differentiation of secondary cultures of normal human prokeratinocytes. Clonal growth was achieved when MCDB 153 was supplemented with epidermal growth factor or wBPE, provided that insulin was present. In the absence of insulin both EGF and wBPE are required. It is mentioned that optimal clonal growth occurred in medium containing 10 ng/ml of epidermal growth factor and 0.3 mM calcium.

According to U.S. Pat. No. 4,673,649, compositions are suggested for clonal growth of a population of human keratinocyte cells in a primary culture for the repair of injury to skin, having a characteristic colony-forming efficiency of about 20%. The composition comprises: MCDB 153, epidermal growth factor a concentration range of 1.0 ng/ml to 25 ng/ml and insulin at a concentration range of 0.5 ug/ml to 50 ug/ml. Optionally, the compositions may contain wBPE (whole bovine pituitary extract) at a concentration range of 7 ug/ml to 700 ug/ml, ethanolamine, hydrocortisone, phosphoethanolamine and calcium chloride. In particular, the compositions are useful for growing skin cells for grafting. No mention is made of the possible use of the disclosed compositions to treat wound conditions in vivo, nor to prolong and preserve the viability of stored split skin grafts. In a very recent U.S. Pat. No. 4,940,666 (by the same inventors and as a c.i.p. of the previous U.S. Patent), the same compositions are claimed to be useful for growing a population of human epidermal cells. The purpose of the compositions suggested is for the propagation of skin cells and achieving monolayers, or stratified layers, of keratinocytes to be used for areas on the body without skin. In other words, these compositions are used for the development of cultured skin cells which may be used for grafting. In addition to the above references, other prior art references suggest that epidermal growth factor may enhance wound healing by increasing fibroblast proliferation.

OBJECTS OF THE PRESENT INVENTION

It is an object of the present invention to provide novel compositions and methods useful for accelerating wound healing.

It is another object of the present invention to provide novel compositions and methods which accelerate wound healing and which also prolong the viability of the skin and other tissues.

It is yet another object of the present invention to provide novel compositions useful for accelerating wound healing which comprise defined and readily recognized constituents.

It is still a further object of the present invention to provide wound healing compositions and methods which accelerate wound healing by maintaining moisture at the wound surface.

It is still a further object of the present invention to provide wound healing compositions and methods which maintain moisture at the wound surface and promote wound healing through use of polymer delivery systems.

These and other objects of the present invention may be readily gleaned from the description of the present invention presented hereinbelow.

BRIEF DESCRIPTION OF THE INVENTION

The present invention relates to formulations and methods for treating wounds utilizing these formulations. The formulations according to the present invention are useful for treating wounds by accelerating wound healing. These formulations comprise an effective amount of a non-steroidal anabolic hormone selected from insulin, triiodothyronine/thyroxine ($T_3$ or $T4)_4$, mixtures thereof, and optionally, growth hormone, most preferably a mixture of all three hormones because of the synergistic effect these three hormones exhibit in combination to promote wound healing, the hormones being further combined with an effective amount of a cellular nutrient medium, preferably a serum free cellular nutrient medium as at least a minimum essential medium, and optionally, at least one cellular growth factor or transforming factor such as insulin-like growth factor (IGF), platelet-derived growth factor (PDGF), epidermal growth factor (EGF) and transforming growth factor (TGF).

In preferred embodiments according to the present invention, the non-steroidal anabolic hormone is insulin. In further preferred embodiments, the formulations also include triiodothyronine ($T_3$), thyroxine or growth hormone along with insulin as the anabolic hormone. In most preferred embodiments according to the present invention, the anabolic hormone comprises a mixture of an effective amount of insulin, growth hormone and triiodothyronine/thyroxine. Embodiments in which the anabolic hormone is a mixture of effective amounts of triiodothyronine/thyroxine and growth hormone or growth hormone and insulin are also contemplated by the present invention.

In general, insulin is included in compositions according to the present invention at concentrations ranging from about 5 ng/ml (nanograms per milliliter) to about 100 ug/ml (micrograms per milliliter) [corresponding to about 120 uUnits/ml (micro Units per ml) to about $24 \times 10^5$ uUnits/ml—approximately 0.0000005% to about 0.01% by weight], preferably about 500 ng/ml to about 5–10 ug/ml (about $1.2 \times 10^4$ uUnits/ml to about $1.2 \times 10^5$ uUnits/ml—about 0.00005% to about 0.0005% by weight of the wound treatment compositions based upon the assumption that 1 ml of solution is equal to about 1 gram in weight). It is noted that the amount of insulin as other components of the instant invention may be modified according to the length of storage time prior to use. When a non-steroidal anabolic hormone other than insulin is included in compositions according to the present invention, for example, triiodothyronine, thyroxine or human growth hormone, among others, each hormone is included in an effective amount of at least about 0.05 ng/ml of the formulation, with a preferred range of about 0.5 ng/ml to about 50 ng/ml or more (generally, up to about 100 ng/ml or more in the case of thyroxine). In compositions which are delivered in solid or concentrated form, i.e. as a gel, creme, elixir, powder or the like, the anabolic hormone is included in concentrations similar to those contained in the solutions, and preferably comprises about 0.00000005% to about 0.000005% by weight of the wound treatment composition (based upon the general assumption that 1 ml of solution is approximately equal to about 1 gram in weight of the final composition). Percent weights may fall outside of these ranges, depending upon the wound treated, the level of stability of the hormone and other factors, as well recognized by one of ordinary skill in the art.

In addition to insulin, the compositions according to the present invention generally include at least one anabolic hormone selected from triiodothyronine or thyroxine and growth hormone, most preferably both growth hormone and triiodothyronine or thyroxine. When growth hormone is used, the preferred growth hormone is human growth hormone, either with triiodothyronine ($T_3$) or preferably in combination with both insulin and triiodothyronine ($T_3$). The preferred amount of anabolic hormone other than insulin used will generally depend on the type and size of the wound, but generally and in most of the cases will be in the range of between about 0.5 ng/ml to about 50 ng/ml by weight or more of the composition (usually no more than about 100 ng/ml. within this range). Of course, one of ordinary skill in the art will recognize that the addition of higher quantities of anabolic hormones (other than insulin-which is generally used in amounts up to about 100 ug/ml.) above 100 ng/ml may be used, especially where the formulations are to be used after a period of storage (components used in the present invention may become less active over time). In the case of compositions which are delivered in solid or concentrated form as a gel, cream, elixir, powder or the like, growth hormone, preferably human growth hormone, is included in an amount ranging from about 0.5 ng/ml to about 50 ng/ml by weight or more (about 0.00000005% to about 0.000005% by weight of the wound treatment composition). Triiodothyronine ($T_3$) is generally preferred over thyroxine because it has greater potency and the same general activity as thyroxine. In instances where storage stability becomes a major concern, the substitution of thyroxione ($T_4$) for triiodothyronine ($T_3$) in the compositions may be merited. In cases where thyroxine is substituted for triiodothyronine, the amount of thyroxine included is generally about 3–5 times the amount of triiodothyronine used in order to provide the same relative degree of activity.

DETAILED DESCRIPTION OF THE INVENTION

Figure 1:
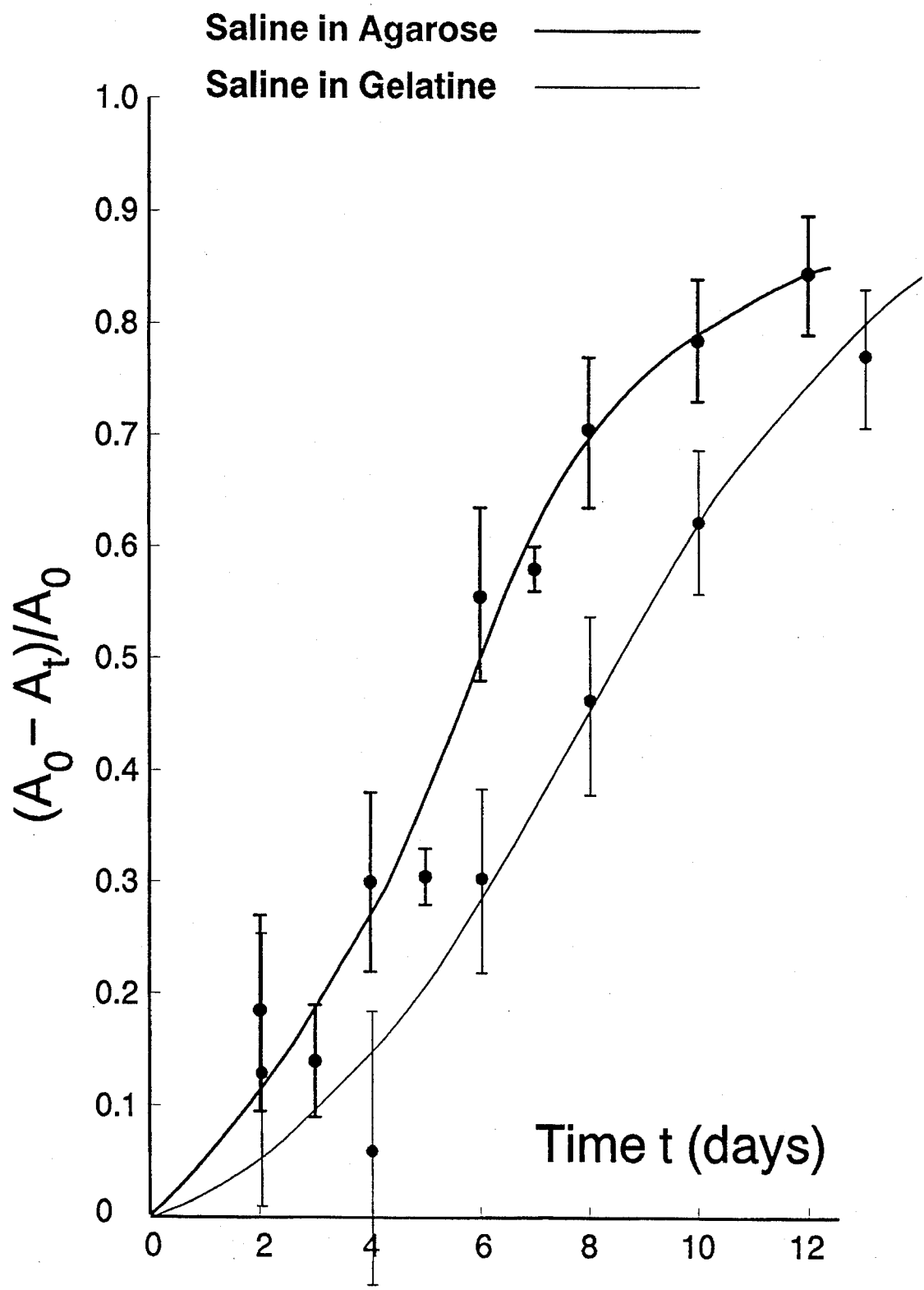
FIGS. 1–15 represent the results of the experiments performed and described in Examples 5–17. These graphs show the fractional change in area of wounds treated with gel-media+hormones vs. various controls. $A_o$ represents the initial wound area and $A_t$ represents the wound area at day t.

In describing the present invention in the specification, a number of terms will be used.

The term "wound" is used throughout the specification to describe skin wounds which are treated by the formulations and the method according to the present invention. A skin wound is defined herein as a breach in the continuity of skin tissue which is caused by direct injury to the skin. Skin wounds are generally characterized by several classes: punctures, incisions, including those produced by a variety of surgical procedures, excisions, lacerations, abrasions, atrophic skin or necrotic wounds and burns, including large burn areas. The formulations according to the present invention are useful in varying degrees for enhancing the healing of all wounds of the skin, including those which occur after a mesh autograph procedure.

The term "delivery polymer" is used throughout the specification to describe a polymer which can be used in combination with a cellular nutrient medium (preferably, serum free), a non-steroidal anabolic hormone selected from insulin, triiodothyronine, thyroxine, growth hormone and mixtures thereof, and optionally, a cellular growth factor or transforming factor to produce formulations which are preferably used for topical administration to treat wounds according to the present invention. These delivery polymers include, for example, numerous hydrogels in hydrated or unhydrated form, such as those derived from hydroxyethylmethacrylate (HEMA), glycerolmethacrylate (GMA) and polyvinylpyrrolidone (PVP), polyethylene glycol (PEG), various carbohydrates, cellulose and related hydrophilic cellulose polymers, dextran, polyethyleneoxide, dextran-polyethylene, acrylamide, polyacrylamide, amylose, collagen, gelatin, sepharose, agarose (for example, as an agarose saturated gel), related polymers and mixtures thereof, among numerous others. One of ordinary skill in the art will recognize to vary the type and amount of delivery polymer in compositions according to the present invention to provide enhanced wound healing characteristics appropriate for topical delivery. The term delivery polymer is also used to describe polymers which instill slow-release or sustained release characteristics to the wound healing formulations of the invention. The term "gelling agent" is used to describe those polymers which may be included in aqueous formulations according to the present invention in effective amounts to gel these formulations.

The term "serum free cellular nutrient medium" or "serum free cellular nutrient mixture" is used throughout the specification to describe a medium or mixture (generally, at least a minimum essential medium) which contains no serum, and in combination with at least one anabolic hormone, preferably at least two anabolic hormones and optionally, at least one cellular growth factor or transforming factor comprises the wound healing compositions according to the present invention. The serum free nutrient medium according to the present invention comprises the following elements: (a) essential amino acids; (b) non-essential amino acids; (c) vitamins selected from the group consisting of biotin, folate, lipoate, niacinamide, pantothenate, pyridoxine, riboflavin, thiamin and vitamin $B_{12}$ and mixtures thereof, preferably a vitamin mixture comprising folate, niacinamide, pantothenate, pyridoxine, riboflavin and thiamin; (d) glucose; and (e) a mixture of inorganic ions selected from the group consisting of calcium, sodium, potassium, magnesium, chloride and mixtures thereof, preferably a mixture comprising calcium, sodium, potassium, magnesium and chloride. All of these elements (a), (b), (c), (d) and (e) are included with the anabolic hormone and optionally the cellular growth factor or transforming factor in concentrations and/or amounts effective for enhancing the growth of cells which surround, have been injured by or are responsible for healing a wound. The preferred concentration of essential and non-essential amino acids used in the present invention ranges from about 5.0 um ($10^{-6}$ mole) to about 50 mmol. ($10^{-3}$ Mole) The preferred concentrations of vitamins used in the present invention ranges from about 1 nanomole ($10^{-9}$ mol.) to about 10 um. The preferred concentrations of glucose used in the invention ranges from about 1 umol. to about 10 or more mmol. In the case of element (e), these inorganic ions are preferably included in the present compositions at a concentration range of about 1 umol to about 50 mmol.

In addition to the elements (a), (b), (c), (d) and (e), the nutrient medium according to the present invention optionally contains any one or more of the following elements: (f) purines and pyrimidines; (g) other organic compounds; (h) other inorganic ions; (i) trace elements; (j) buffers and indicators and (k) other supplements. All of the optional elements (f), (g), (h), (i), (j) and (k), when they are included in the nutrient medium according to the present invention, are included in amounts effective for enhancing the growth of cells involved in the wound-healing processes in combination with the anabolic hormone(s). Preferably, components (f), (g), (j) and (k) range in concentration from about 1 nmol. to about 10 mmol. In the case of components (h) and (j), the concentration preferably ranges from about 1 umol. to about 50 mmol. One of ordinary skill in the art will be able to readily modify the type and amount of the components of the cellular nutrient medium within the teachings of the present invention.

In addition to serum free cellular nutrient medium, the present invention may also make use of cellular nutrient medium containing serum, although the use of a serum containing cellular nutrient medium is generally less preferred than is serum free medium. Examples of such nutrient medium include, among numerous others, DMEM, HAM F12 and HAM F10, all containing serum. The term "cellular nutrient medium" "nutrient medium" or "nutrient mixture" is used to describe all types of nutrient medium contemplated for use in the present invention which contain at least the basic elements (generally, of a minimum essential medium) as described hereinabove, and such term includes serum free cellular nutrient medium.

The cellular nutrient medium according to the present invention may include one or more commercially available media in solution or lyophilate (solid) form. The cellular nutrient medium used may be in the form of a lyophilate which may be reconstituted with water, preferably sterilized, distilled water and then supplemented with an anabolic hormone such as insulin, triiodothyronine, thyroxine, growth hormone or mixtures thereof, and optionally, at least one cellular growth factor or transforming factor or other additive. Alternatively, the nutrient medium may be used directly in formulations according to the present invention in the form of a lyophilate, or related solid-type material, rather than a solution, especially when gels, creams, elixirs, powders or other delivery vehicles are to be used for delivery. It is clearly preferred when utilizing solid-type materials for delivering the wound healing compositions according to the present invention that the delivery system in the form of a hydrogel or other form contain moistening quantities of water.

Many of the commercially available media (preferably, serum free) are available from suppliers such as Collaborative Research Incorporated, Bedford, Mass., GIBCO, Grand Island, N.Y., USA or Biological Industries, Beth HaEmek, Israel. These media may be used as purchased or modified within the scope and practice of the present invention.

The term "cellular growth factor" "cellular transforming factor" or "transforming factor" is used throughout the specification to describe those compounds other than the anabolic hormones which are optionally added to the formulations according to the present invention for their known benefits in stimulating the growth and elaboration of cells. Cellular growth factors or transforming factors for use in the present invention include for example, epithelial growth factor (EGF), platelet derived growth factor (PDGF), transforming growth factor (TGF) and insulin-like growth factor (IGF), among others. In certain preferred formulations according to the present invention, one or more cellular growth factor or transforming factor is included in combination with at least one anabolic hormone, most preferably a combination of effective amounts of insulin, triiodothyronine and growth hormone in an amount effective for stimulating the growth of cells and skin which surround, have been injured by or are responsible for healing a wound. Cellular growth factors or transforming factors for use in the present invention may include naturally isolated or synthetically produced versions of the above-mentioned compounds or their equivalents and include, where relevant, compounds produced by genetic engineering processes and techniques.

The term "non-steroidal anabolic hormone" is used throughout the specification to describe the primary hormones which are included in the instant invention to promote wound healing in combination with cellular nutrient media. These primary hormones include insulin, triiodothyronine, thyroxine, and growth hormone among others. When growth hormone is used, it is preferred to use it in combination with triiodothyronine/thyroxine or insulin or most preferably with a mixture of triiodothyronine/thyroxine and insulin. As used herein, the term non-steroidal anabolic hormone includes naturally isolated (preferably, human) or synthetically produced versions of these hormones which are known to function substantially the same as the naturally occurring hormones and includes, where relevant, compounds produced by genetic engineering processes and techniques. Insulin is an especially preferred non-steroidal anabolic hormone. While not being limited by way of theory, it is believed that the inclusion of at least one non-steroidal anabolic hormone selected from insulin and triiodothyronine or thyroxine, and preferably at least two or more anabolic hormones selected from insulin, triiodothyronine or thyroxine and growth hormone, serves to enhance the effect of the nutrient media in increasing the rate of natural wound healing. Thus, it is believed that the non-steroidal anabolic hormone actually enables the wounded cells to utilize or process the nutrients in the media, which action results in an enhanced rate of wound healing.

The amount of each component which is used in the formulations according to the present invention will depend upon the type and size of the wound, but each component preferably is included in an amount effective for significantly enhancing the healing of a wound relative to traditional wound healing therapies. In general, in embodiments according to the present invention, the formulations include an anabolic hormone other than insulin at a concentration of at least about 0.05 ng/ml, preferably about 0.5 ng/ml to about 50 ng/ml or more, more preferably about 0.5 ng/ml to about 20 ng/ml or more. In the case of formulations containing insulin, the amount of insulin generally falls outside of this range, because of its tendency to degrade and become inactivated at a more rapid rate than the other anabolic hormones. Stabilized forms of insulin could obviously be used at concentrations outside of the above range. Preferably, the anabolic hormone is insulin and/or growth hormone and is most preferably insulin because of the known benefits these hormones have in promoting the growth and elaboration of cells and their general absence of toxicity.

The preferred anabolic hormone is insulin in combination with either triiodothyronine, thyroxine or growth hormone. The preferred insulin is human insulin, which is a well-known protein which is readily available commercially from a number of sources (for example, Sigma Chemical Co., USA or Novo Nordisk, Copenhagen, Denmark). It is constituted from a number of amino acids (approximately 51) with a total molecular weight of about 5,500. Human insulin for use in the present invention is generally prepared using genetic engineering techniques. Depending upon the manufacturer, the insulin may have slightly different activity based upon weight, however the activity of insulin defined in units is, of course, standard. While not being limited by way of theory, in the present invention, it is believed that the insulin promotes wound healing by enhancing the transport and utilization of glucose by the cells.

Growth hormone may also be used in the present invention, either alone or preferably in combination with insulin or triiodothyronine/thyroxine and most preferably in combination with both triiodothyronine/thyroxine and insulin. The preferred human growth hormone is a well-known defined protein which is readily available and results from a pituitary secretion into the blood system. It is constituted from a number of amino acids with a total molecular weight of about 193,000. The human growth hormone which may be used in the present invention can be obtained from a variety of sources, including genetic engineering processes and techniques. While not being limited by way of theory, it is believed that the growth hormone stimulates fibrinogenesis, i.e., the synthesis of growth factors which also may exhibit some favorable influence on the rate of wound healing.

The present invention also contemplates the inclusion of effective amounts of triiodothyronine/thyroxine either alone or in combination with other non-steroidal anabolic hormones. The preferred triiodothyronine is human triiodothyronine, which is a well-known defined hormone and readily available commercially. Triiodothyronine and thyroxine are naturally occurring amino acids of the thyroid gland which exert a stimulating effect on metabolism. Although virtually identical in metabolic effects, triiodothyronine is more potent than is thyroxine and is preferred for use in the present invention. While not being limited by way of theory, it is believed that the triiodothyronine or thyroxine utilized in the present invention stimulates vascularization and facilitates the resupply of blood borne components. It is further believed that $T_3/T_4$ may promote the dissociation of oxygen from hemoglobin and may also contribute to tissue growth and regeneration by making oxygen more readily available.

A particularly preferred composition according to the present invention comprises a mixture of an effective amount of human growth hormone in the presence of an effective amount of insulin (transferrin containing or transferrin-free) and triiodothyronine ($T_3$) or thyroxine ($T_4$), preferably in a serum free cellular nutrient medium. In this preferred embodiment of the instant invention, the anabolic hormones other than insulin, i.e., growth hormone and/or triiodothyronine/thyroxine are generally included in the final composition in a concentration range of about 0.05 ng/ml to about 50 ng/ml, preferably about 0.5 ng/ml to about 20 ng/ml. In this preferred embodiment, insulin is also included in an effective amount, generally an amount which is substantially greater than the other anabolic hormones because of its tendency to rapidly degrade or become inactive after being placed on a wound. The amount of insulin is preferably included in amounts ranging from about 5 ng/ml to about 100 ug/ml (about 120 uU/ml to about 2.4 Units/ml, depending upon the manufacturer of the insulin), preferably about 500 ng/ml to about 5 ug/ml. One of ordinary skill in the art will know to vary the amount of anabolic hormones within effective ranges based upon the type and potency of the preparation of the compound.

The present invention may also optionally include a cellular growth factor or transforming factor in addition to one or more non-steroidal anabolic hormones. Each cellular growth factor or transforming factor is included in the final composition in an effective amount, i.e., an amount generally ranging from about 0.05 to about 50 ng/ml or higher concentration, and preferably about 1 ng/ml to about 20 ng/ml or more of the final composition.

In certain embodiments according to the present invention a wound healing composition comprises an effective amount of a cellular growth factor or transforming factor in cellular nutrient medium. PDGF and IGF are preferred growth factors for use in the present invention, with PGDF being most preferred.

The cellular nutrient medium which is used in the present invention is any nutrient medium having the effect of enhancing recovery of wounded or atrophic skin tissue when used in combination with the cell growth stimulating compound. In preferred embodiments according to the present invention, the nutrient media is comprised of the componentry set forth hereinabove, is mixed with a wound healing effective amount of the non-steroidal anabolic hormone to form the compositions according to the present invention.

The cellular nutrient medium comprises effective amounts of the following constituents: (a) essential amino acids; (b) non-essential amino acids; (c) vitamins as previously described; (d) inorganic ions as previously described and (e) glucose; and optionally, (f) purines and pyrimidines; (g) other organic compounds; (h) other inorganic ions; (i) trace elements; (j) buffers and indicators and (k) other supplements. Preferably, the cellular nutrient medium used herein contains effective amounts of elements (f) through (k). Serum free nutrient medium is preferred. The preferred serum free nutrient medium is modified MCDB, a well-known medium. Mixtures of standard commercial nutrient media may also be used with favorable results in the instant invention.

While not being limited by way of theory, it is believed that one plausible explanation of the mechanism of the accelerated wound healing is that the presence of the anabolic hormone, and in particular, insulin and/or triiodothyroine/thyroxine and/or human growth hormone (preferably a mixture of at least two of these anabolic hormones and most preferably a combination of insulin, triiodothyronine or thyroxine and growth hormone) in the formulations according to the present invention, promotes the utilization of the nutrients from the nutrient medium and consequently, growth in situ of the granulation tissue, i.e., within the wound itself. At the same time, the novel formulations may also induce the stimulation of the vascular elements and promote the growth of vascularized granulation tissue preparatory to split skin grafting. The present formulations may in this same way also be useful to promote the healing, growth and regeneration of atrophic skin and to function as atrophic skin adjuvants. The proliferation of vascularized granulation promotes epidermal growth from the peripheral edges of the wound over the vascular substratum and from deeper layers of the dermis leading to an early closure of the skin over the wound. The mechanism which might be assumed is that during the proliferation phase, new capillaries and fibroblasts appear in the wound from the first day on and reach their maximum levels after one week. The new vessels in granulation tissue originate as budlike structures on nearby vessels, penetrate the wound, become canalized and ramify throughout the wound by cellular division.

It is further believed that the function of the nutrient medium is to provide nutrients to normal, distressed and injured cells and skin which surround or comprise the wound to be treated in order to enhance the growth and repair mechanisms which are responsible for the healing of the wound. In this way, the nutrient medium functions with the non-steroidal anabolic hormone to promote the normal processes of elaboration, growth and healing of the wound and adjacent skin areas. In addition, the media serves to maintain a moist environment surrounding the wound area.

A number of nutrient media, preferably serum free, alone or in combination, may be used in the present invention, including commercially available media or other media well known in the art. Examples of such media (all without serum or having had the serum removed) include ADC-1, LPM (Bovine Serum Albumin-free), F10 (HAM), F12 (HAM), DCCM1, DCCM2, RPMI 1640, BGJ Medium (Fitton-Jackson Modification), Basal Medium Eagle (BME-with the addition of Earle's salt base), Dulbecco's Modified Eagle Medium (DMEM-without serum), Glasgow Modification Eagle Medium (GMEM), Leibovitz L-15 Medium, McCoy's 5 A Medium, Medium M199 (M199E-with Earle's salt base), Medium M199 (M199H- with Hank's salt base), Minimum Essential Medium Eagle (MEM-E- with Earle's salt base), Minimum Essential Medium Eagle (MEM-H- with Hank's salt base) and Minimum Essential Medium Eagle (MEM-NAA- with non-essential amino acids), among numerous others. These and other useful serum-free nutrient media are available from GIBCO, Grand Island, N.Y., USA and Biological Industries, Bet HaEmek, Israel, among others.

In addition, serum-containing nutrient media may also be used in compositions according to the present invention, but the use of serum-containing media is less preferred because of the possibility that the serum may be contaminated with microbial agents and because the patient may develop immunological reactions to certain antigenic components contained in the serum.

While a large number of serum free nutrient media may be used in the present invention, a preferred nutrient media for use in the present invention is modified MCDB 153.

Experiments which were carried out to prolong the viability of human split skin graft specimens show that the use of the modified MCDB 153 medium in compositions according to the present invention, extended the limit of viability from 3 to 9 weeks. Histological examination of the skin specimens indicated a strong attachment of the epidermal layer to the dermal substratum in all specimens kept in the modified MCDB 153 medium at 4°–8° C.

Hereafter are enumerated the particular constituents and concentrations of the above groups for MCDB 153:

|  | Concentration in M |
| --- | --- |
| Group (a): | |
| Arginine | $1.0 \times 10^{-3}$ |
| Cysteine or Cystine | $2.4 \times 10^{-4}$ |
| Glutamine | $6.0 \times 10^{-3}$ |
| Histidine | $8.0 \times 10^{-5}$ |
| Isoleucine | $1.5 \times 10^{-5}$ |
| Leucine | $5.0 \times 10^{-4}$ |
| Lysine | $1.0 \times 10^{-4}$ |
| Methionine | $3.0 \times 10^{-5}$ |
| Phenylalanine | $3.0 \times 10^{-5}$ |
| Threonine | $1.0 \times 10^{-4}$ |
| Tryptophan | $1.5 \times 10^{-5}$ |
| Tyrosine | $1.5 \times 10^{-5}$ |
| Valine | $3.0 \times 10^{-4}$ |
| Group (b): | |
| Alanine | $1.0 \times 10^{-4}$ |
| Asparagine | $1.0 \times 10^{-4}$ |
| Aspartate | $3.0 \times 10^{-4}$ |
| Glutamate | $1.0 \times 10^{-4}$ |
| Glycine | $1.0 \times 10^{-4}$ |
| Proline | $3.0 \times 10^{-4}$ |
| Serine | $6.0 \times 10^{-4}$ |
| Group (c): | |
| Biotin | $6.0 \times 10^{-8}$ |
| Folate | $1.8 \times 10^{-6}$ |
| Lipoate | $1.0 \times 10^{-6}$ |
| Niacinamide | $3.0 \times 10^{-7}$ |
| Pantothenate | $1.0 \times 10^{-6}$ |
| Pyridoxine | $3.0 \times 10^{-7}$ |
| Riboflavin | $1.0 \times 10^{-7}$ |
| Thiamin | $1.0 \times 10^{-6}$ |
| Vitamin B12 | $3.0 \times 10^{-7}$ |

-continued

| | Concentration in M |
|---|---|
| Group (d) | |
| Glucose | $6.0 \times 10^{-3}$ |
| Group (e): | |
| Magnesium | $6.0 \times 10^{-4}$ |
| Postassium | $1.5 \times 10^{-3}$ |
| Sodium | $1.5 \times 10^{-1}$ |
| Chloride | $1.3 \times 10^{-1}$ |
| Calcium | 0.1 mmol. |
| Group (f): | |
| Adenine | $1.8 \times 10^{-4}$ |
| Thymidine | $3.0 \times 10^{-6}$ |
| Group (g): | |
| Acetate | $3.7 \times 10^{-3}$ |
| Choline | $1.0 \times 10^{-4}$ |
| i-Inositol | $1.0 \times 10^{-4}$ |
| Putrescine | $1.0 \times 10^{-6}$ |
| Pyruvate | $5.0 \times 10^{-4}$ |
| Group (h) | |
| Phosphate | $2.0 \times 10^{-3}$ |
| Sulfate | $4.5 \times 10^{-6}$ |
| Group (i): | |
| Copper | $1.0 \times 10^{-8}$ |
| Iron | $1.5 \times 10^{-6}$ |
| Zinc | $3.0 \times 10^{-6}$ |
| Group (j): | |
| Bicarbonate | $1.4 \times 10^{-2}$ |
| HEPES | $2.8 \times 10^{-2}$ |
| Group (k): | |
| Ethanolamine | 0.1 mmol. |
| Phosphoethanolamine | 0.1 mmol. |

Weights of each of the above components in the medium may be varied within the concentrations described hereinabove to provide formulations workable within the description of the present invention.

Preferably, the non-steroidal anabolic hormone to be incorporated into the modified MCDB 153 composition, according to the present invention, is a mixture of two hormones selected from insulin, triiodothyronine/thyronine and growth hormone at effective concentrations. Most preferably, the anabolic hormone includes a mixture of human growth hormone, insulin (containing transferrin or transferrin-free) and triiodothyronine ($T_3$) or thyroxin ($T_4$), each hormone included in an effective amount for promoting wound healing. Hormones other than insulin are included in an amount ranging from at least about 0.05 ng/ml, preferably at least about 0.5 ng/ml to about 20 ng/ml. In the case of insulin, the effective amount of insulin generally ranges from about 5 ng/ml to about 100 ug/ml and more preferably about 500 ng/ml to about 5 ug/ml within this range. Higher amounts of insulin may be merited where the formulation is to be stored for longer periods of time.

In addition to effective amounts of non-steroidal anabolic hormones and cellular nutrient media and optionally, effective amounts of at least one cellular growth factor or transforming factor, formulations according to the present invention may also advantageously contain ascorbic acid, which in certain instances may have a beneficial overall effect in enhancing wound healing because of its ability to function as a reducing agent. Transferrin (which is believed to improve iron transport) in amounts which preferably range from about 500 ng/ml to about 50 ug/ml, more preferably about 5 ug/ml and selenite (preferably, in the form of sodium selenite) in amounts preferably ranging from about 0.5 to about 50 ng/ml, more preferably about 5 ng/ml, may also be optionally included in the present formulations.

Insulin (including transferrin or transferrin-free) is a desirable constituent anabolic hormone, found to impart a maturing stimulus of the growing culture. Insulin may be commercially obtained and is generally provided in mU quantities (about 41 ng of insulin). The International Unit of Insulin (SI=System International) is the activity contained in 0.04167 mg (41.67 ug) of the 4th International Standard Preparation (1958). The Standard Preparation is a quantity of purified Zinc Insulin crystals extracted 52% from Bovine and 48% from Porcine pancreas (See, Martindale Pharmacopoeia, 26th Ed.).

The formulations according to the present invention may also include an effective amount of an antimicrobial agent, for example, antibiotics, antiviral and antifungal agents, such as griseofulvin and nystatin, and the like. The antimicrobial agent may be added for its ability to treat an infection, or alternatively, for its prophylactic effect in avoiding an infection. Where antimicrobial agents are contemplated for use in the present invention, an amount effective to treat an infection or a prophylactic amount of such agent is chosen. The amount of antimicrobial agent used is that amount typically used in topical applications. One of ordinary skill in the art can easily determine the type and amount of antimicrobial agent chosen for use in formulations according to the present invention.

In general, the amount of antimicrobial agent may vary widely according to the efficacy of the agent to be delivered and the prophylactic treatment or the severity of the infection. However, in general, the amount of antimicrobial agent to be used in the present invention will range from about 0.05 ug/ml to about 250 mg/ml with a preferred range of about 50 to about 200 ug/ml. Of course, these ranges will vary depending upon the condition of the infection to be treated as well as the strength of the antimicrobial agent employed. For example, in the case of treatment of fungal infections, the amount of amphotericin used generally ranges from about 0.1 ug/ml to about 100 ug/ml with a preferred concentration of about 0.25 ug/ml. In the case of antibiotics and in particular, penicillin, streptomycin and gentamycin, these agents are generally utilized within the concentration range of about 0.05 ug/ml to about 250 mg/ml. with a preferred concentration range of about 25 ug/ml to about 250 ug/ml.

In the case of the use of antibiotics, any number of antibiotics may be used, including aminoglycosides, sulfa drugs, penicillins and chloramphenicol, among others, but it is preferable to use the broad spectrum antibiotics, for example, a cephalosporin or tetracycline in a prophylactic amount or alternatively, in an amount effective for treating a bacterial infection. In using antibiotics, one of ordinary skill in the art will recognize to minimize or avoid the use of antibiotics which may produce allergic reactions in the treated patients.

In certain embodiments according to the present invention, the formulations as described herein are further formulated with hydrogels or related delivery polymers for delivering the formulations according to the present invention to the wound. In these embodiments, the formulations comprising effective amounts of anabolic hormone(s) and nutrient media, either alone or in addition to other optional components, are admixed with amounts of a delivery polymer effective for producing a gel, for example a hydrogel polymer derived from HEMA (hydroxyethylmethacrylate)

or NVP (N-vinylpyrrolidone), polyethylene glycol (PEG), polyethylene, gelatin, various carbohydrates, sepharose, agarose, methylcellulose, hydroxymethyl and hydroxyethylcellulose and related hydrophilic cellulose polymers including cellulose, dextran, polyethyleneoxide, dextran-polyethylene, acrylamide, polyacrylamide, amylose or collagen to promote wound healing and skin growth. In general, the amount of delivery polymer which is added to the formulations to produce a gel generally ranges from about 0.1% by weight to about 20% by weight, preferably about 1% to about 5% or more by weight, depending upon the type of delivery polymer used. The gel compositions according to the present invention preferably contain sufficient water or moisture to maintain the wound area in a moist state—a condition shown to be beneficial to wound healing. In addition to accelerating wound healing through application of the formulations of the present invention, the compositions which are formulated with a delivery polymer also exhibit the added benefit of preventing or slowing the formation of a scab on the wound. While not being limited by way of theory, it is believed that the resultant wound tissue, which remains soft and moist instead of dry and scab-like, produces a beneficial, cosmetically pleasing and increased rate wound-healing.

In addition to solution, gel or hydrogel forms, compositions according to the present invention also may be formulated as creams, elixirs, powders and the like. The various components of the wound treatment compositions according to the present invention may have to be varied in order to maintain effective concentrations for promoting wound healing. When wound healing compositions according to the present invention are formulated, these compositions may also contain an amount of a pharmaceutically acceptable excipient and, in addition, other additives such as diluents, compounding agents, bulking agents, surfactants and the like. One of ordinary skill in the art will recognize to vary the concentrations of the individual components as a function of the type of delivery vehicle used for the wound treatment compositions in order to facilitate and enhance the wound healing activity of the present formulations.

In a method for treating wounds according to the present invention, the formulations as described hereinabove are topically applied to the wound tissue as a liquid or gel preferably at least once a day and up to six or more times a day. In the case of formulations containing a delivery polymer, preferably a moistened delivery polymer, the formulations may be administered less frequently than when the formulations are applied as a liquid, for example, once every several days or more. One of ordinary skill in the art will readily be able to determine the amount and frequency of administering the formulations according to the present invention.

The amount of material which is to be spread on a wound for treatment will be readily apparent to one of ordinary skill in the art. In general, in solution or gel form, about 1 cc of formulation is applied per cm$^2$ to the wound area. Depending upon the depth of the wound to be treated, an amount greater or less than 1 cc of formulation per cm$^2$ of the wound surface may be utilized. In many instances, the depth of the formulation on the wound should be at least about 2 mm.

Preliminary bioassays to determine the acceleration of wound healing which were carried out on rats, guinea pigs and on selected clinical cases indicated that the formulations according to the present invention exhibited a significant beneficial result relative to traditional therapies.

The invention will be described hereinafter by a number of Examples which illustrate some actual tests carried out on wounds treated with the compositions according to the present invention. It should be understood that the Examples are not exhaustive nor limiting and are presented only for a better understanding of the invention.

EXAMPLES

Example 1

Wound-Healing Formulation 100 g. of Lyophilized powder of MCDB 153 was reconstituted with distilled, sterilized H$_2$O and supplemented with human growth hormone to a final concentration of about 0.5 to about 2 ng/ml by conventional mixing. In certain formulations, an amount of insulin-transferrin was added to a final concentration of about 5 ug/ml. The resulting solution was used to treat wounds as exemplified by the following wound-treatment examples. In certain instances, about 1% by weight gelatin or collagen was added to provide a gel product for delivery to wounds as indicated.

Example 2

Heel Decubitus-pressure wound

A woman suffering from an acute Toxic Epidemolysis Necrosis (TEN), due to hypersensitivity to sulfa medication developed an oval shape pressure wound (10×5×2 cm) on her right heel. Conservative treatment failed to produce a successful result.

First treatment consisted of the application of a liquid composition of the formulation according to the present invention containing 1.0 ng/ml of human growth hormone and covered by a bandage.

Three days later, the bandage, stained with exudate which had seeped through, was removed. Proliferation of granulation tissue was noticed in the wound bed. The initial oval-shaped contour of the boundary was now keyhole-shaped, having a reduced size of 7×3×1 cm. A similar treatment with the same composition as above was applied on the wound.

Three days later, the bandage was found to be dried and was removed. The wound appeared to be substantially narrowed and had a size of 5×1.5×0.5 cm. The granulation tissue in the wound was highly vascularized. A similar treatment with the same composition as above was applied. Three days later the dry bandage was removed and the wound was found to be completely closed.

Example 3

Old chronic leg wound

A 16 month old chronic tapered-oval-shaped crural ulcer (7×3.5×2 cm) was located on the anterior aspect of the upper third tibia. A conventional treatment which was applied was repeatedly unsuccessful.

A collagen gel of the composition according to Example 1 containing 0.5 ng/ml of growth human hormone was applied and covered by a bandage.

Three days later, the exudate-stained bandage was removed. Granulation tissue and vascularization were clearly noticed in the wound bed. The size of the wound was found to be 5.5×2.5×1 cm and its contour was rounded-oval-shaped. A second treatment with the same collagen gel of the modified MCDB 153 composition as above was applied.

Four days later, the bandage was removed; the wound bed revealed highly vascularized granulation tissue. The wound had an oval shape and its size was 4×2×0.5 cm. Three days later, the bandage was removed. The wound had a spindle shape with a size of 3×1.×0.25 cm. The same collagen gel treatment as above was applied. Four days later, the bandage was removed and the size of the wound was found to be 2.5×1×0 cm.

After a few days the patient informed that the wound was completely closed.

Example 4

A wound caused by a recurrent crural ulcer was treated. The ulcer wound (10×7.1×1.5cm) did not respond to any conventional treatment.

In the first treatment a solution of Example 1 containing 2 ng/ml of human growth hormone and 5 ug/ml of Insulin was applied.

A week later, the fibril exudate-stained bandage was removed. A considerable granulation tissue proliferation was noticed that raised the bed of the wound. The size of the wound was found to be 8×5×0.5 cm. The wound was washed with a solution (3% by vol.) of hydrogen peroxide and the same solution as in the first treatment was applied.

Four days later, the bandage was removed and it was noticed that granulation tissue filled most of the gap of the wound which was clean.

A split-skin graft was further applied.

Examples 5–17

In the following examples 5–17, modified serum-free culture medium was supplemented with non-steroidal anabolic hormones and tested for its wound-healing activity versus numerous controls. The medium was prepared in a purified 1% alginate gel matrix and in 4% gelatin to which physiological concentrations of growth hormone, thyroxin and insulin/transferrin were added.

Under general anaesthesia of Katamin, four 2×3 cm full-thickness skin patches were surgically extirpated from the dorsum of Hartley-derived guinea pigs. After application of the gel (about 1 cc/cm$^2$) to the wounds, the wounds were dressed with Omiderm, a polyurethane-based synthetic wound dressing (Omikron, Israel) and anchored with gauze and elastic adhesive bandage. Change of the bandages and administration of the gels were performed every 48 hours, under general anaesthesia, at which time in one group, the wounds were washed with ESDC disinfectant (Symbollon Corp., Mass., USA), washed with warm saline, measured and photographed. Computerized morphometric measurements of the photographs were made and the dynamics of the regeneration process were quantified and analyzed. A more detailed description and the results of these experiments is presented herein.

Materials and Methods

1. Preparation of Gel-Media

The whole procedure was performed under sterile conditions.

a. Delivery System

One gram of Agarose Type 1-A; Low EEO (Sigma Chemical Co.) was dissolved in 10 cc of 2×distilled water. The solution was autoclaved. All preparations of the gel media were made using a final concentration of either 1% Agarose or gelatin.

b. Media

The preferred media contained essential and non-essential amino acids, vitamins, other organic constituents, major inorganic salts, trace elements and buffers and was supplemented with CaCl and L-glutamine and with the non-steroidal anabolic hormones, insulin, thyroxin, growth hormone and insulin-like growth factor (IGF) at the concentrations as indicated below.

| Component | Concentration in M |
| --- | --- |
| Amino Acids (L-enantiomers) | |
| Alanine | $1.0 \times 10^{-4}$ |
| Arginine HCl | $1.0 \times 10^{-3}$ |
| Asparagine | $1.0 \times 10^{-4}$ |
| Aspartic Acid | $3.0 \times 10^{-5}$ |
| Cysteine HCl or Cystine | $2.4 \times 10^{-4}$ |
| Glutamic Acid | $1.0 \times 10^{-4}$ |
| Glutamine | $6.0 \times 10^{-3}$ |
| Glycine | $1.0 \times 10^{-4}$ |
| Histidine HCl | $6.0 \times 10^{-5}$ |
| Isoleucine | $1.5 \times 10^{-5}$ |
| Leucine | $5.0 \times 10^{-4}$ |
| Lysine HCl | $1.0 \times 10^{-4}$ |
| Methionine | $3.0 \times 10^{-5}$ |
| Phenylalanine | $3.0 \times 10^{-5}$ |
| Proline | $3.0 \times 10^{-4}$ |
| Serine | $6.0 \times 10^{-4}$ |
| Threonine | $1.0 \times 10^{-4}$ |
| Tryptophan | $1.5 \times 10^{-5}$ |
| Tyrosine | $1.5 \times 10^{-5}$ |
| Valine | $3.0 \times 10^{-4}$ |
| Vitamins | |
| d-Biotin | $6.0 \times 10^{-8}$ |
| Folic Acid | $1.8 \times 10^{-6}$ |
| DL-a-lipoic acid | $1.0 \times 10^{-6}$ |
| Niacinamide | $3.0 \times 10^{-7}$ |
| D-pantothenate 1/20a | $1.0 \times 10^{-6}$ |
| Pyridoxine HCl | $3.0 \times 10^{-7}$ |
| Riboflavin | $1.0 \times 10^{-7}$ |
| Thiamin HCl | $1.0 \times 10^{-6}$ |
| Vitamin B12 | $3.0 \times 10^{-7}$ |
| Other Organic Constituents | |
| Acetate | $3.7 \times 10^{-3}$ |
| Adenine | $1.8 \times 10^{-4}$ |
| Choline chloride | $1.0 \times 10^{-4}$ |
| D-glucose | $6.0 \times 10^{-4}$ |
| i-Inositol | $1.0 \times 10^{-4}$ |
| Putrescine 2HCl | $1.0 \times 10^{-6}$ |
| Na Pyruvate | $5.0 \times 10^{-4}$ |
| Thymidine | $3.0 \times 10^{-6}$ |
| Major Inorganic Salts | |
| $CaCl_2$ | $4.0 \times 10^{-5}$ |
| KCl | $1.5 \times 10^{-3}$ |
| $MgCl_2$ | $6.0 \times 10^{-4}$ |
| NaCl | $1.2 \times 10^{-1}$ |
| $Na_2HPO_4$ | $2.0 \times 10^{-3}$ |
| Trace Elements | |
| $CuSO_4$ | $1.1 \times 10^{-8}$ |
| $FeSO_4$ | $5.0 \times 10^{-6}$ |
| $H_2SeO_3$ | $3.0 \times 10^{-8}$ |
| $MnSO_4$ | $1.0 \times 10^{-9}$ |
| $Na_2SiO_3$ | $5.0 \times 10^{-7}$ |
| $(NH_4)_6Mo_7O_{24}$ | $1.0 \times 10^{-9}$ |
| $NH_4VO_3$ | $5.0 \times 10^{-9}$ |
| $NiCl_2$ | $5.0 \times 10^{-10}$ |
| $SnCl_2$ | $5.0 \times 10^{-10}$ |
| $ZnSO_4$ | $5.0 \times 10^{-7}$ |
| Buffers | |
| Hepes | $2.8 \times 10^{-2}$ |
| $NaHCO_3$ | $1.4 \times 10^{-2}$ |

-continued

| Component | Concentration in M |
|---|---|
| Non-Steroidal Anabolic Hormones | |
| Human Growth Hormone | 2–5 ng/ml |
| Insulin/Transferrin & sodium selenite | 5 ug/ml Insulin 5 ug/ml Transferrin 5 ng/ml Na selenite |
| Triiodothyronine ($T_3$) | $2.0 \times 10^{-8}$ (13.02 ng/ml) |
| Insulin-like Growth Factor (IGF) | 8, 16 or 24 ng/ml |
| Vehicle | |
| Agarose (Sigma – A 0169) EEO (Electroendosmosis 0.10–0.15) Gel Point – 36° C. Melting Point – 87° C. Gel Strength – >825 g/cm² for 1% pH 7–8.5 | 1% | c. Preparation of Wound Healing Formulation

Ninety cc of the above-defined media was warmed in a water bath to 40° C. Following autoclaving, 10 cc of a 1% agarose gel solution was allowed to cool to 40° C. and the solution was then added to the media to produce a homogeneous mixture. The mixture was thereafter aspirated into 10 and 20 cc syringes and refrigerated at 4° C.

2. Animal Model for Studies

Hartley-derived Albino guinea pigs weighing 300–400 grams were used in this study. The animals were housed in individual cages and fed regularly guinea pig chow and water enriched with Vitamin C ad libitum. All surgical procedures were performed under general anaesthesia using Katamin HCl ([d]-2-(o-chlorophenyl)-2-(methylamino)cyclohexanone hydrochloride, available from Parke-Davis) 150 mg/kg i.m. All histological sections were prepared using Hematoxylene and Eosin stain as well as Mason's trichrome method for collagen.

Each animal was anesthetized and four bilaterally symmetrical full-thickness skin segments measuring 2×3 cm were excised from the dorsum of each animal, two from the scapular region and two from the lumbar region. After washing the wounds with warm saline, the wounds were dressed with the gel at a concentration of about 1 cc/cm², covered with a polyurethane based synthetic membrane Omiderm (Omikron, Israel) and anchored with gauze, elastic adhesive and a Retelast netting (Medinet, s.p.a., Italy). The dressings were changed every 48 hours under general anaesthesia, at which time the wounds were washed with warm saline to remove any debris and the remaining gel within the wound, measured, photographed and fresh gel was applied and the wounds dressed as described above. In one experiment, a disinfectant compress of ESDC (Symbollon, Corp.) was applied during the change of dressing for about ten minutes, preceded and followed by warm saline rinse. At days 4, 6, 8, 10 and 12, the animals were sacrificed and the wounds with the surrounding tissues were extirpated and prepared for histological examination.

The thickness of the newly formed epithelial layer and of the underlying granulation tissue were measured using light microscopy (Zeiss) at 100×magnification.

The wound macrophotographs were analyzed using ImageMeasure (Phoenix Corp., Seattle, Wash.) computerized morphometric program and the experimental results were plotted as graphs showing the fractional change in area (i.e. closure rate) of the wounds treated with gel-media+ hormones versus the various controls. The wound closure rate was tabulated and peak closure day (% closure) was determined.

Peak closure rate has been used as a measure of wound healing potency. Peak closure rate is the maximum slope of the $$\frac{Ao - At}{Ao}$$

vs. time curve. Peak closure rate indicates the time after the start of the treatment at which tissue healing or growth rate reaches a maximum value (maximum rate); i.e., when the treatment is optimal.

Examples 5–17

Eight groups of experiments were performed using various combinations of medicament as controls:

Experiment 1—Gelatin in saline (n=12) vs. Agarose in saline (n=12).

Experiment 2—Test for Controls—Scarlet Red (n=19) and Agarose in saline (n=12) as positive and negative controls respectively vs. Agarose in hormone supplemented medium with insulin/transferrin (5 ug/ml), Triiodothyronine/Thyroxine (about 13.02 ng/ml) and Human Growth Hormone (about 2 ng/ml).

Experiment 3—Agarose in hormone-supplemented medium (n=12) vs. Agarose in medium without hormonal supplement (n=12).

Experiment 4—Agarose with either Insulin/Transferrin (n=33, 5 ug/ml), Triiodothyronine/Thyroxine (n=28, 13.02 ng/ml) or Growth Hormone (n=27, 2 ng/ml) in saline (no medium) vs. medium in Agarose containing all three hormones using the same concentration (n=12) as each of the components specified above.

Experiment 5—Agarose in medium supplemented with the three hormones (n=12) as above vs. Agarose in medium supplemented with either Insulin (n=8), Triiodothyronine/Thyroxine (n=8) or Growth Hormone (n=8).

Experiment 6—Agarose in saline supplemented with the three hormones (n=12) in the concentrations set forth above vs. Agarose in medium supplemented with the three hormones (n=12).

Experiment 7—Agarose in 3 hormone-supplemented medium (as above, n=12) without a disinfectant compress vs. the same medicament plus a 10 minute compress of ESDC disinfectant (Symbollon Corp.) applied during the change of bandages (n=15).

Experiment 8—Agarose in medium supplemented with either Insulin (n=12), Triiodothyronine/Thyroxine (n=12) or Growth Hormone (n=12) vs. Agarose in saline supplemented with Insulin (n=12), Growth Hormone (n=12) or Triiodothyronine/Thyroxine (n=12).

Experiment 9—Agarose in medium supplemented with Insulin and Triiodothyronine/Thyroxine (n=12) and Triiodothyronine/Thyroxine and Growth Hormone (n=12) vs. Agarose in saline supplemented with Insulin and Triiodothyronine/Thyroxine (n=12) and Triiodothyronine/Thyroxine and Growth Hormone (n=12).

Experiment 10—Agarose in medium supplemented with Insulin (n=12) vs. Agarose in medium supplemented with IGF at 8 ng/ml. (n=12).

Experiment 11—Agarose in medium supplemented with Insulin, Triiodothyronine/Thyroxine and Growth Hormone (n=12) vs. Agarose in medium supplemented with IGF at 8 ng/ml, Triiodothyronine/Thyroxine and Growth Hormone (n=12).

Experiment 12—Agarose in medium supplemented with Triiodothyronine/Thyroxine, Growth Hormone and varying concentrations of IGF (IGF at 8 ng/ml, 16 ng/ml and 24 ng/ml).

Experiment 13—Agarose in medium supplemented with IGF at 8 ng/ml vs. Agarose in saline supplemented with IGF at 8 ng/ml.

Example 5

Test for Formulation Delivery Vehicle

Gelatin and Agarose were prepared in saline and the two gels were used to treat experimental wounds. The rate of closure of the wounds treated with Agarose was faster than the rate of closure of wounds treated with gelatin. (See FIG. 1).

Wound closure rate comparison indicates that the closure of 50% was 31% faster with Agarose in Saline as compared to Gelatin in Saline. Peak closure rate occurred 33% earlier with Agarose in Saline treatment. (See Table 1, set forth below).

Example 6

Test for Positive and Negative Controls

Figure 2:
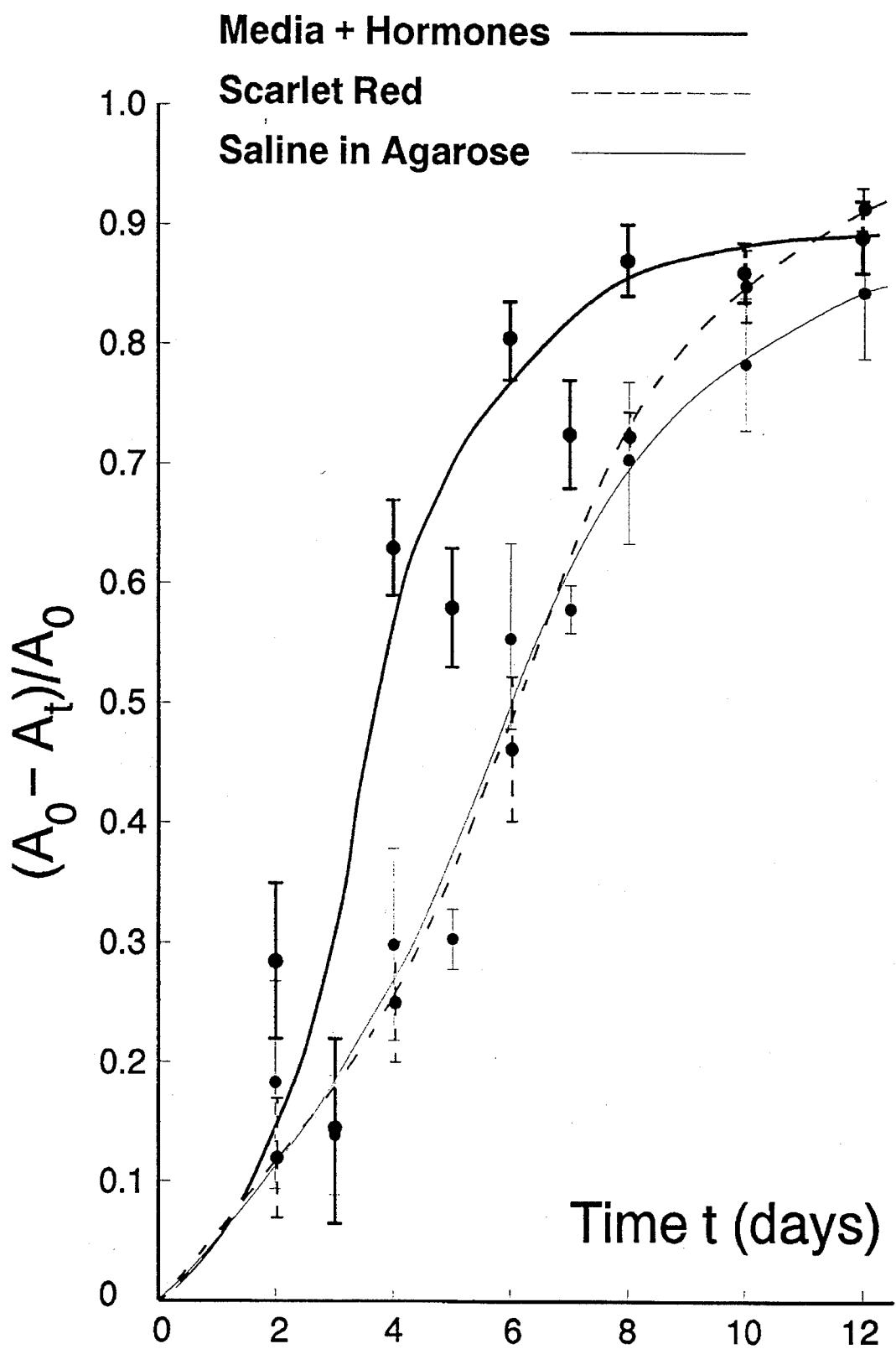

Scarlet red dressing (0-Tolylazo-0Tolylazi-beta-naphthol plus lanolin, olive oil and petroleum from Chesebrough-Ponds, Inc., Hospital Products Division, Greenwich, Conn., USA-an azo dye-containing preparation routinely used in hospitals and claimed to increase epitheliazation) was used a positive control and Saline in Agarose was used as a negative control. The rate of wound closure for each of these formulations was plotted against that of the wounds treated with media+hormones (n=15). Comparison of wound closure rate indicates that 50% closure was 50% faster with media+hormone treatment as compared to both controls. (See FIG. 2). Peak closure rate occurred 50% and 40% later for Saline and Scarlet Red treatment, respectively, as compared to media+hormones.

Example 7

Treatment with Media+Hormones in Agarose vs. Media in Agarose Alone

Figure 3:
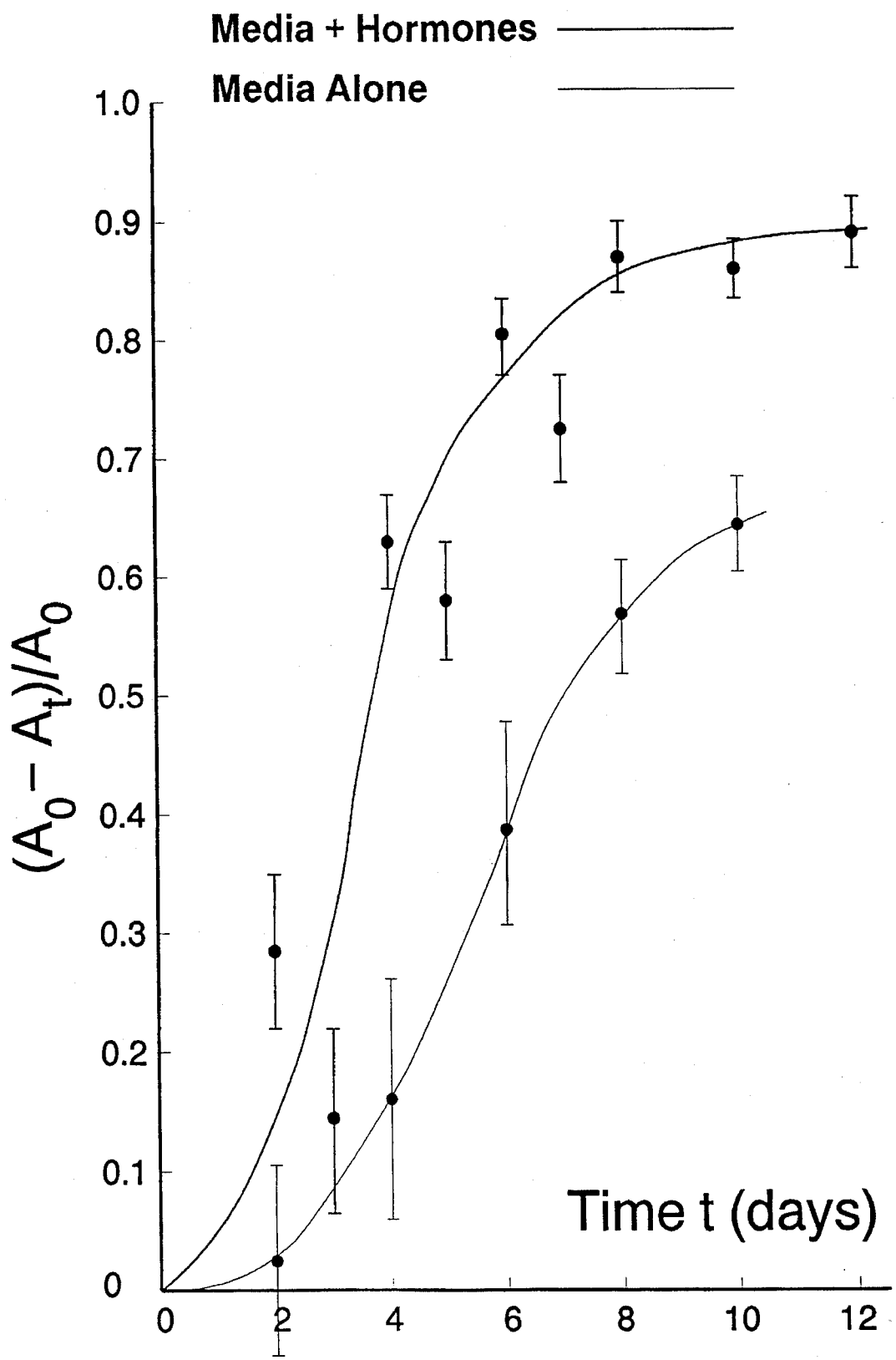

Treatment with the media+3 hormones formulation induced accelerated wound healing compared to treatment with media prepared in Agarose without hormonal supplement (FIG. 3). The rate of wound closure using the media alone was similar to that of the wounds treated with saline in Agarose.

Since media alone did not induce any stimulatory effect on wounds closure, the presence of at least one hormone and preferably three hormones appears essential for utilization of the media by the cells.

Comparison of wound closure rate indicates that closure of 50% was 60% slower with media alone compared to media+3 hormones (Table 1). Peak closure rate occurred 50% earlier in media+3 hormone treated wounds compared to wound treated with media alone.

Example 8

Figure 4:
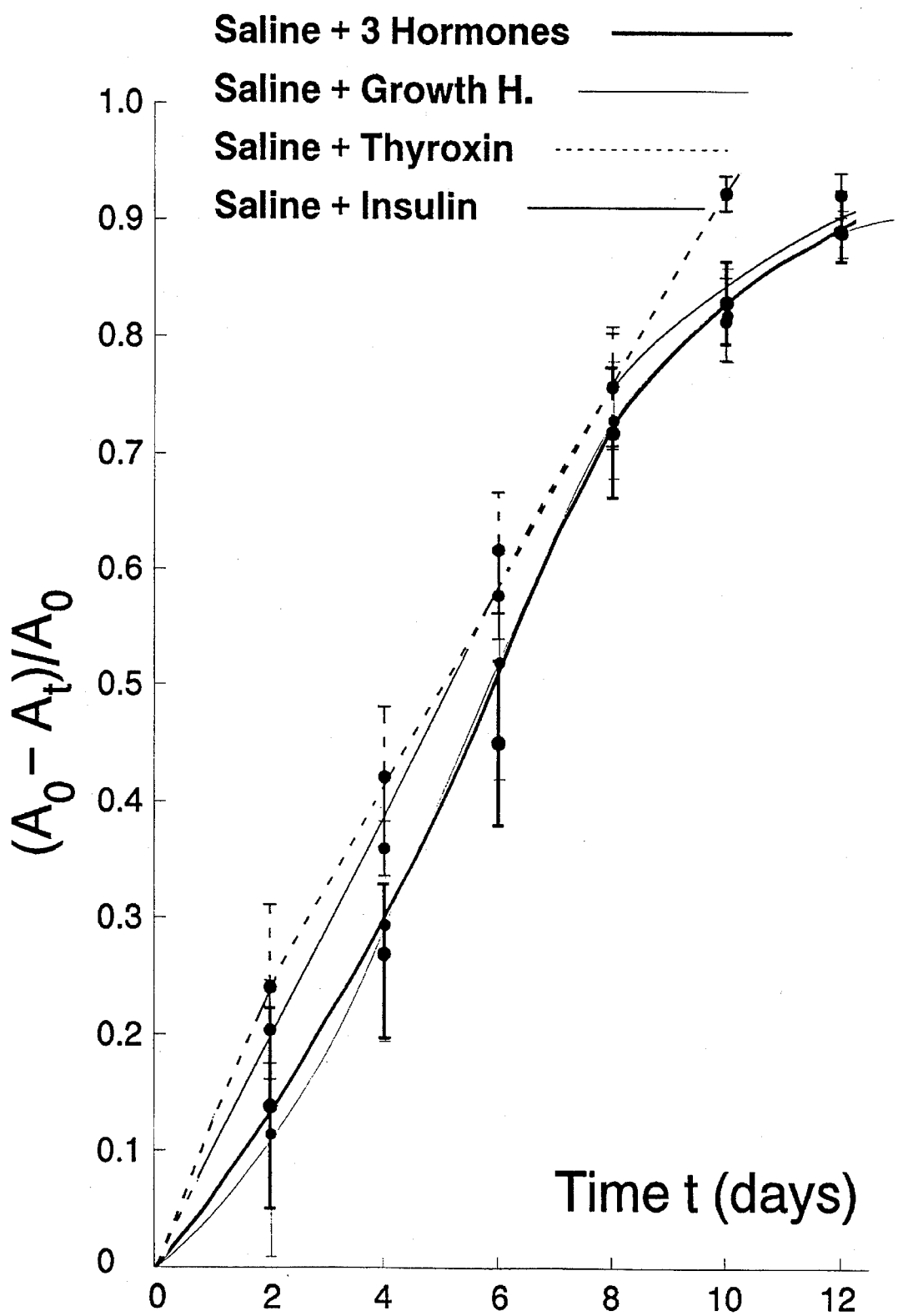

Test of Agarose in Saline (No Medium) Supplemented with either Insulin or Thyroxin or Growth Hormone vs. Treatment with Agarose in Saline Supplemented with the Three Hormones The three hormones together induced a similar rate of growth to treatment with each hormone separately. Thus no synergistic effect was demonstrated by the presence of the three hormones together when mixed with Saline in Agarose (see FIG. 4).

Closure rate of wounds treated with each hormone, Insulin, Thyroxin and Growth Hormone separately, were similar. Comparison of closure rates indicated that the closure of 50% was 15% faster for Insulin and Thyroxin and the same for Growth Hormone and Saline+the three hormones together (See table 1).

Peak closure rate was the same for Insulin, Thyroxin and Growth Hormone as well as for saline+3 hormones.

Example 9

Figure 5:
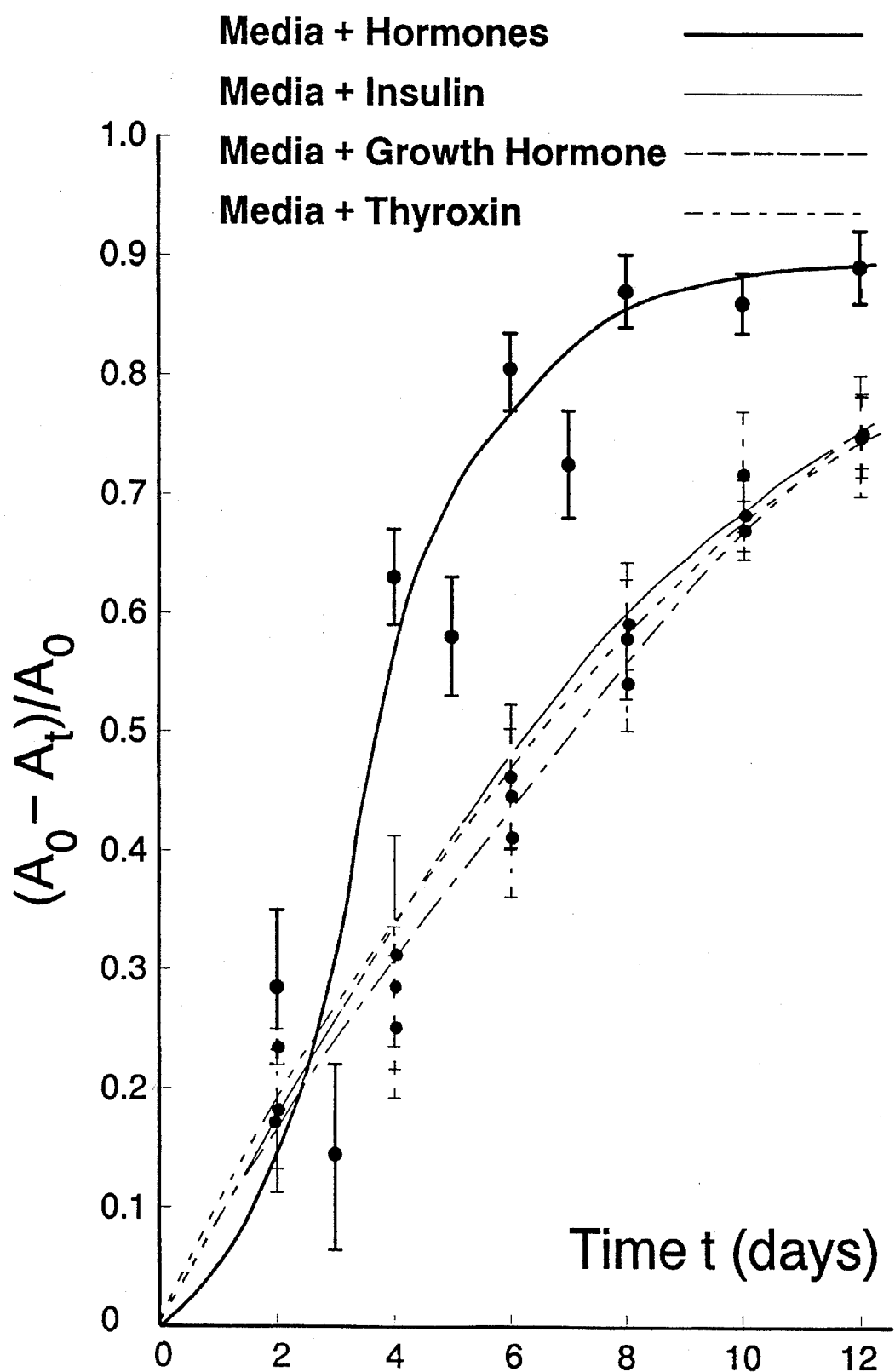

Test of Agarose in Medium Supplemented with 3 Hormones vs. Agarose in Media Supplemented with either Insulin, Thyroxin or Growth Hormone Treatment with Media+3 hormones yielded significantly faster rate of wound closure (See FIG. 5) than Agarose in media supplemented with any one of the three hormones.

Closure rates of wounds treated with media supplemented with one of the hormones, Insulin, Thyroxin and Growth Hormone were similar. However, combination of the three hormones in the media yielded a synergistic effect. Comparison of closure rates indicated that the closure rate of 50% was 75% slower for Insulin, thyroxin and for Growth Hormone compared to the combination of the three hormones. Peak closure rate was roughly the same for Insulin, Thyroxin and Growth Hormone and occurred 33% later than that of Media+3 hormones together.

Example 10

Test of Agarose in Saline+3 Hormones vs. Agarose in Media+3 Hormones

Figure 6:
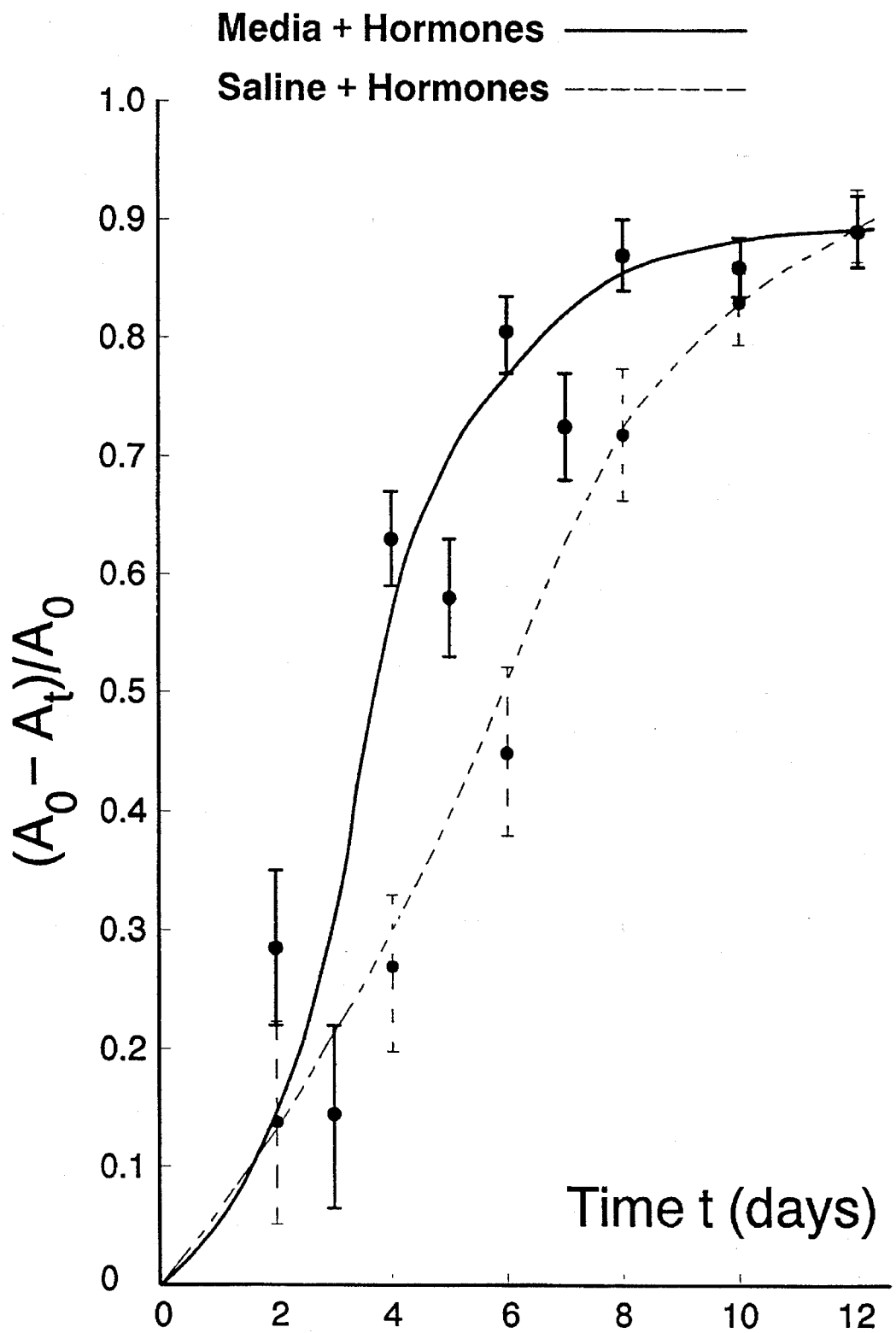

For the first two days the wound closure of both groups was essentially similar. After the second day, however, the rate of wound closure of the group treated with the 3 hormones in saline (without media) was significantly slower than that of the wounds treated with the media+hormones (See FIG. 6).

The presence of media induced a faster rate of wound closure as compared to the rate of the same 3 hormones without the media. Comparison of wound closure rates indicated that the closure of 50% was 86% and slower for the Saline+hormones as compared to the Media+hormones. In addition, peak closure rate occurred 57% earlier in the Media+3 hormones compared to the Saline+3 Hormone treatments.

Example 11

Test of Agarose in Media+3 Hormones with and without ESDC Disinfectant Compress

Figure 7:
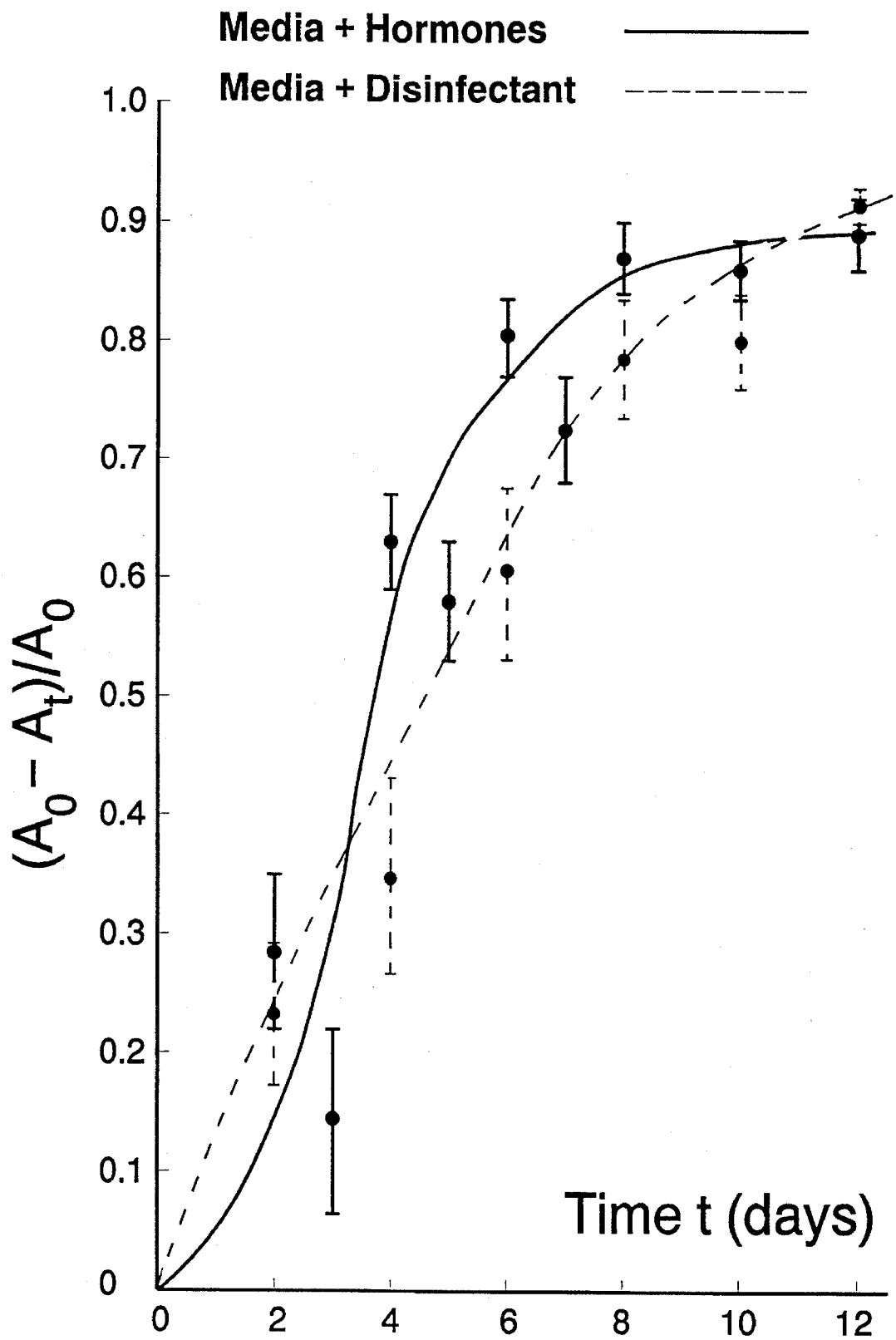

The rate of wound closure with the media+disinfectant treatment was initially faster than that of wounds treated with media alone. However, on the 2nd day the rate of wound closure for wounds treated with media+hormones accelerated and was faster than the closure rate of the wounds treated with the addition of the disinfectant compress. After the initial period of time, the disinfectant exerted a cumulative cytotoxic effect which slowed the healing process. (See FIG. 7).

Comparison of wound closure rate indicated that the closure of 50% was 45% slower with the disinfectant treatment.

Peak closure rate occurred 100% later with the disinfectant treatment compared to the medium+3 hormones without disinfectant treatment.

TABLE 1

Wound Closure Rate Comparison

| Closure % (Day) | 50% | Peak Closure Day (% Closure) |
|---|---|---|
| Media + Hormones | 3.5 | 3.0 (30%) |
| Saline in Agarose | 6.0 | 6.0 (50%) |
| Saline in gelatin | 8.5 | 9.0 (50%) |
| Scarlet Red | 6.0 | 5.0 (35%) |
| Media + Disinfectant | 5.0 | 6.0 (60%) |
| Insulin | 5.0 | 3.0 (30%) |
| Triiodothyronine/thyroxine | 5.0 | 3.0 (30%) |
| Growth Hormone | 6.0 | 6.0 (50%) |
| Media Alone | 7.0 | 6.0 (40%) |
| Saline + Hormones | 7.0 | 7.0 (50%) |

Example 12

Figure 8:
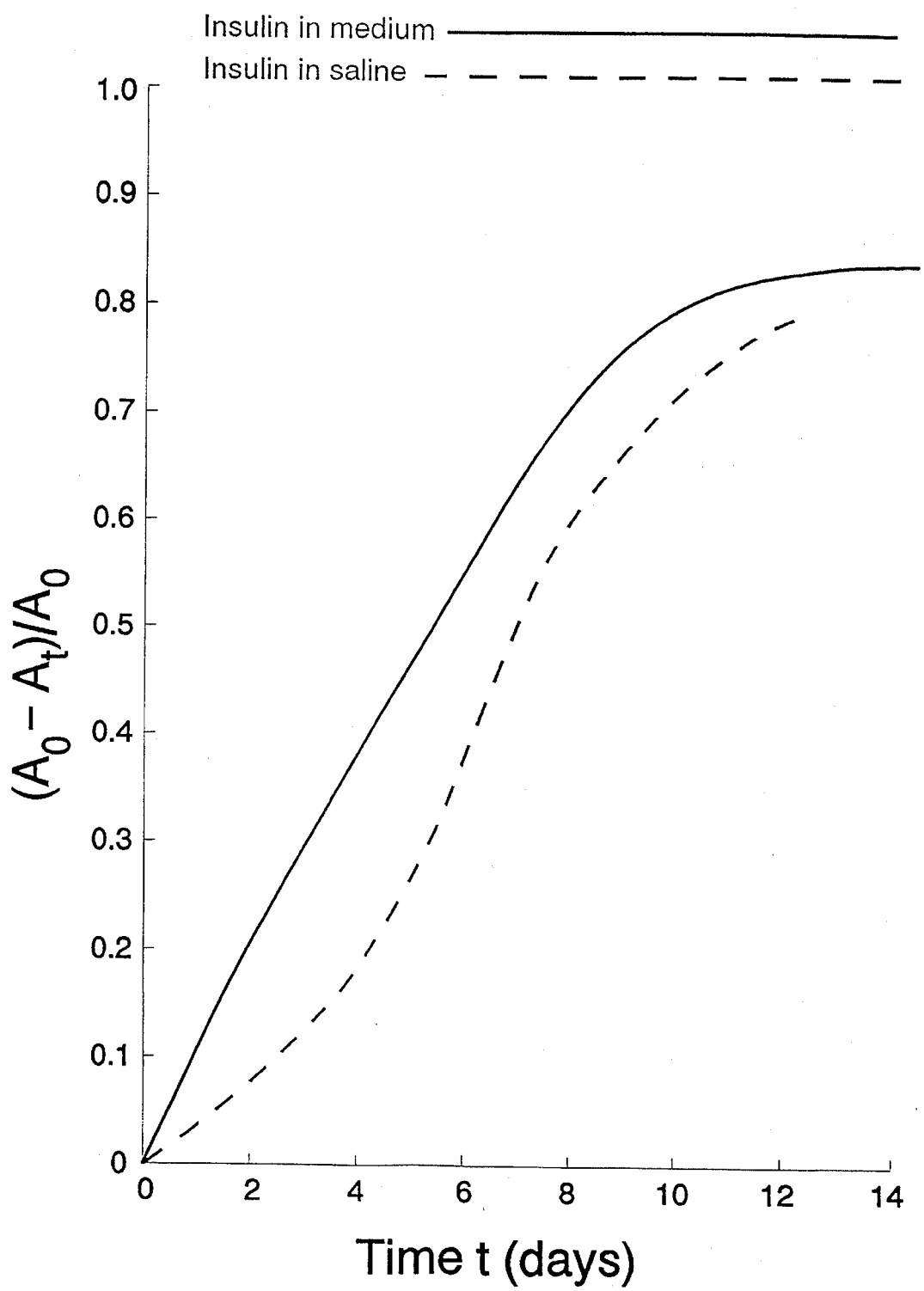
Figure 9:
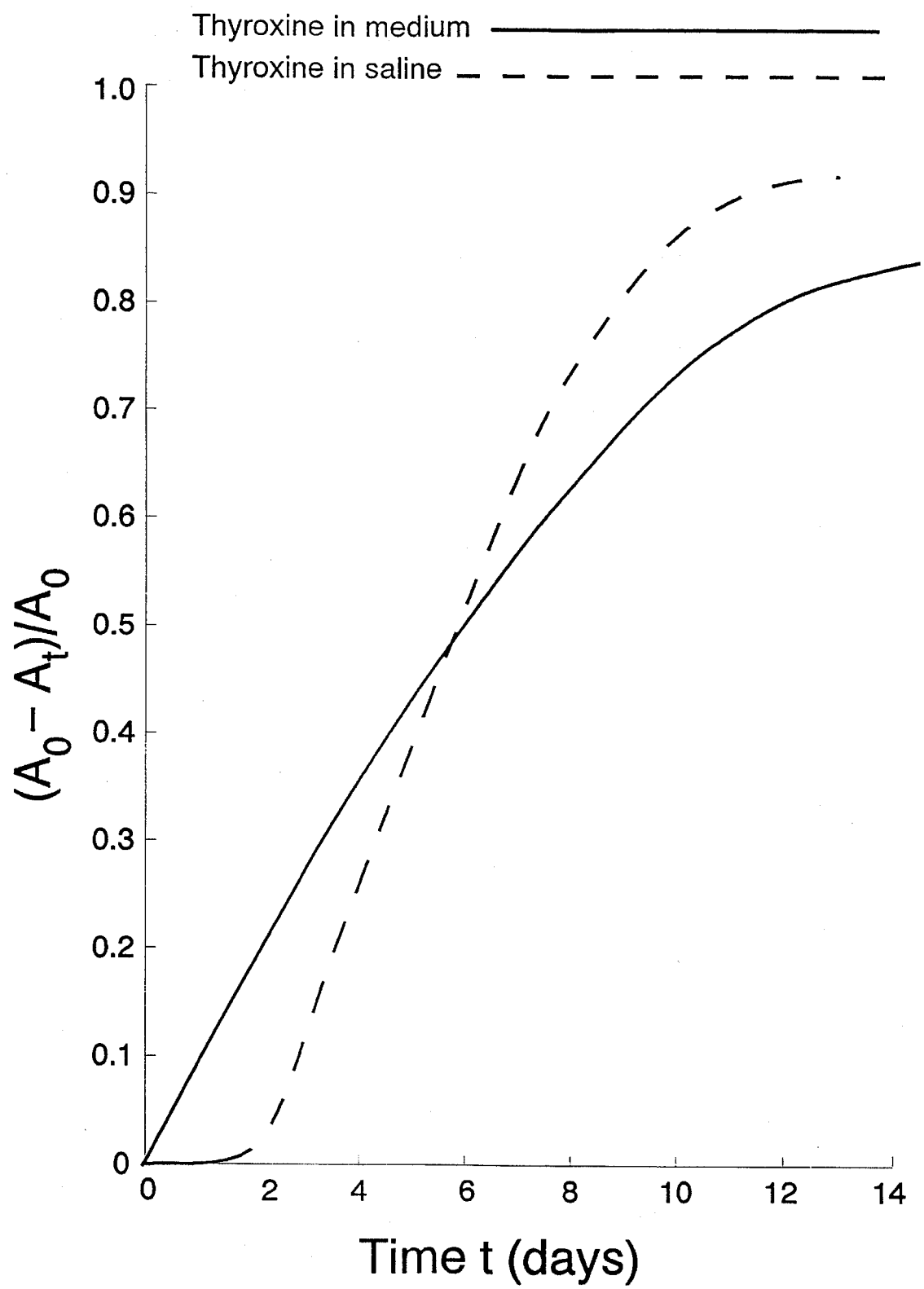

Test of Agarose in Medium Supplemented with Insulin or Triiodothyronine/thyroxine vs. Agarose in Saline Supplemented with Insulin or Triiodothyronine/Thyroxine This experiment was conducted to determine the overall effect that a combination of medium with one hormone would have on wound healing relative to effects of one hormone in saline (without medium). In each case where the wound healing effects of a composition comprising hormone in medium was compared to hormone in saline, the composition containing hormone in medium produced substantially enhanced wound healing activity. This enhanced activity is exhibited by insulin or triiodothyronine/thyroxine in medium. The results for insulin and triiodothyronine/thyroxine are presented in FIGS. 8 and 9, respectively.

Example 13

Figure 10:
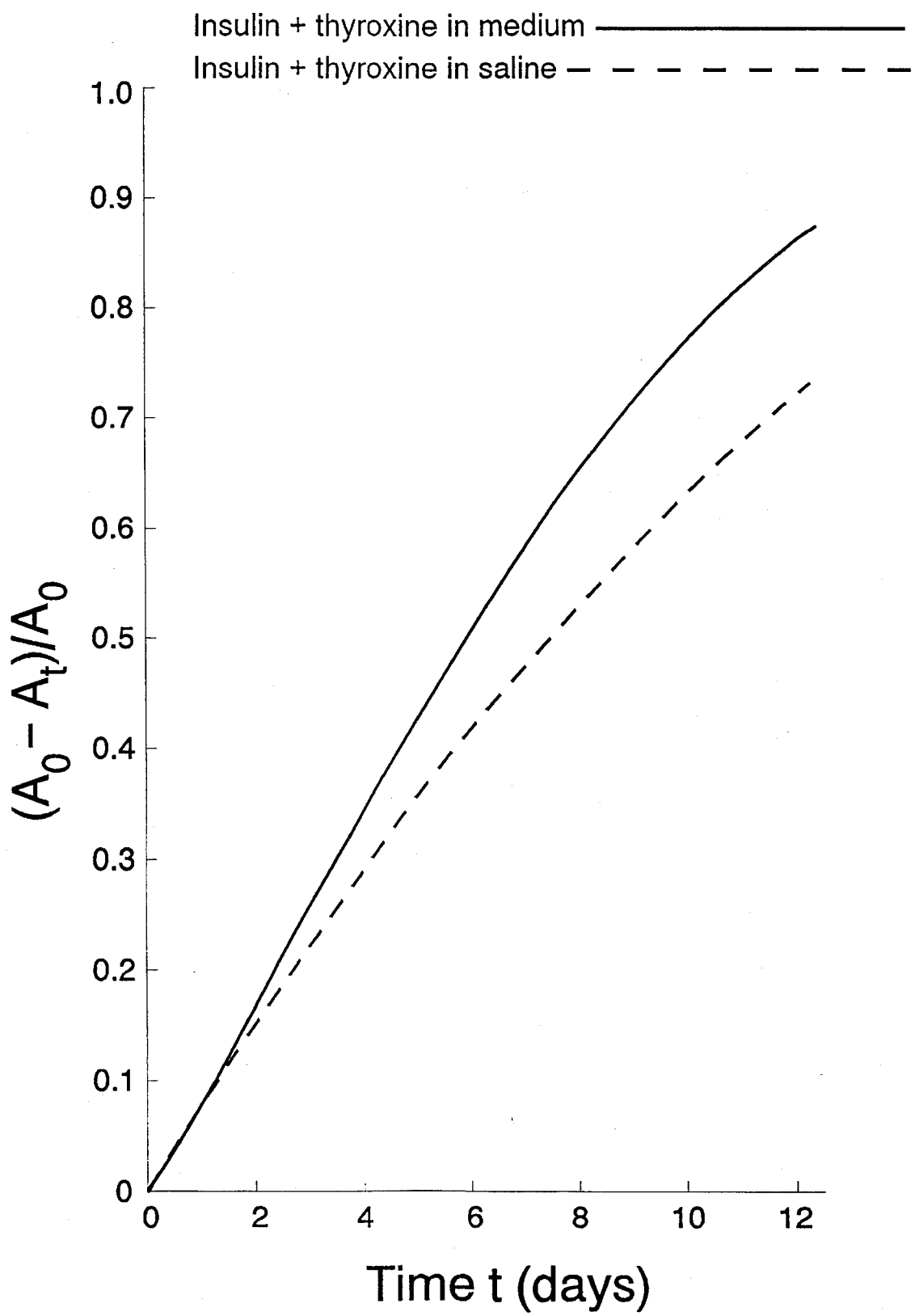
Figure 11:
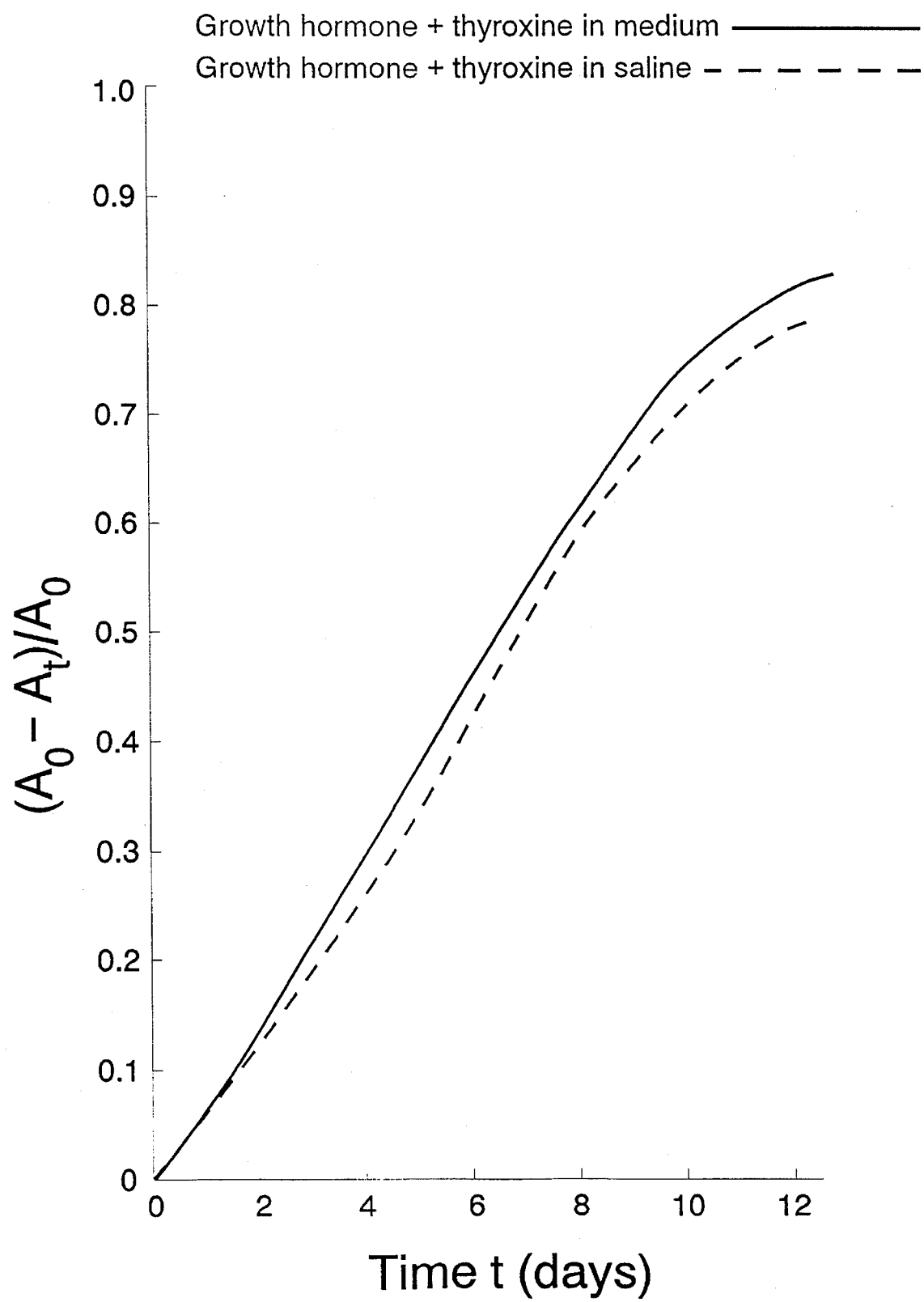

Test of Agarose in Medium Supplemented with Insulin and Triiodothyronine/thyroxine or Growth Hormone and Triiodothyronine/thyroxine vs. Agarose in Saline Supplemented with Insulin and Triiodothyronine/Thyroxine or Growth Hormone and Triiodothyronine/thyronine This experiment was conducted to determine the overall effect that a combination of medium with two hormones would have on wound healing relative to effects of two hormones in saline (without medium). In each case where the wound healing effects of a composition comprising two hormones in medium was compared to two hormones in saline, the composition containing the hormones in medium produced substantially enhanced wound healing activity. This enhanced activity is exhibited by all combinations of two hormones selected from insulin, growth hormone or triiodothyronine/thyroxine in medium, although in the case of insulin and growth hormone, the effect was seen in clinical trials. The results for insulin and triiodothyronine/thyroxine and separately, growth hormone and triiodothyronine/thyroxine are presented in FIGS. 10 and 11, respectively.

Example 14

Figure 12:
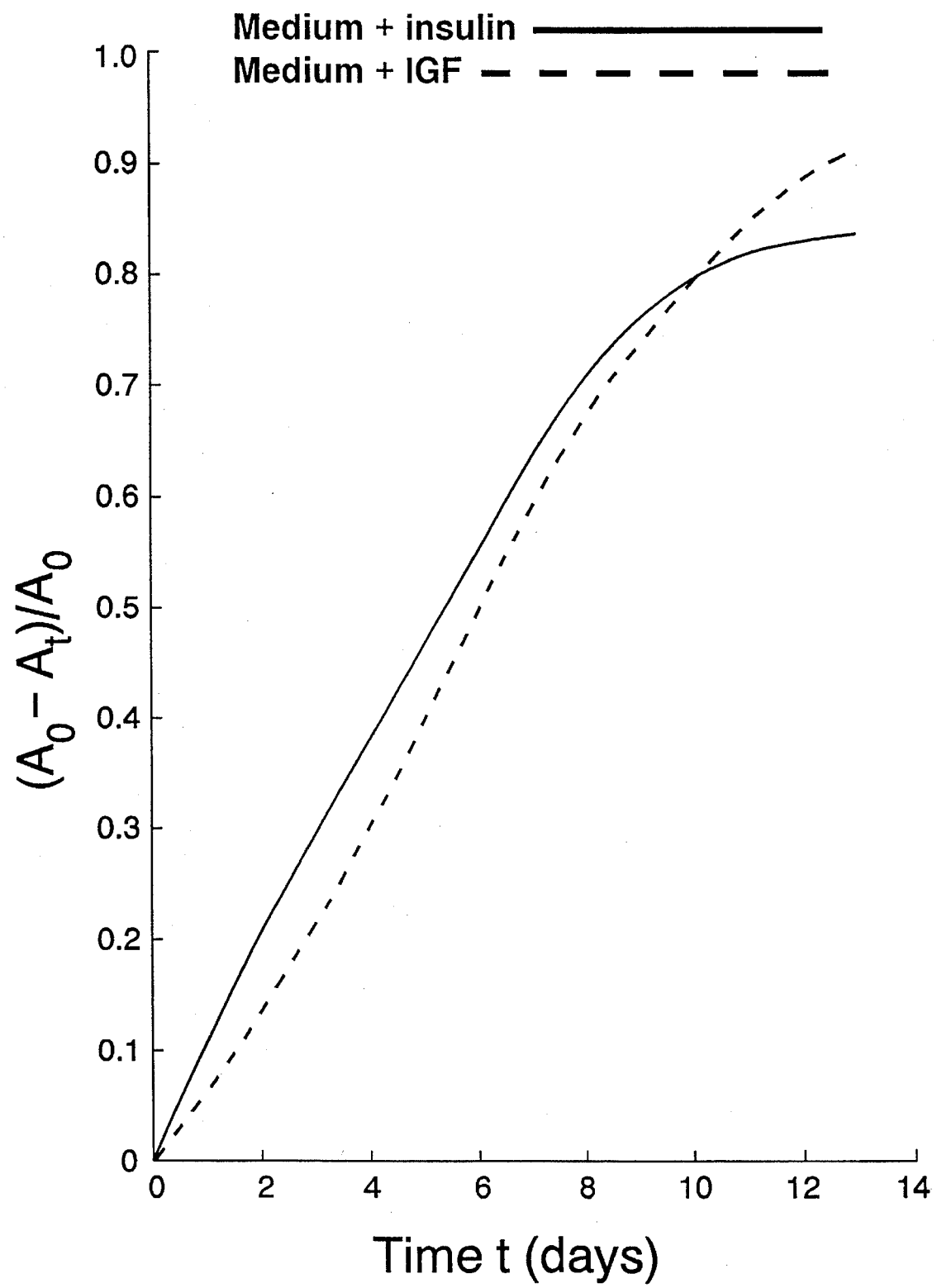

Agarose in Medium Supplemented with Insulin vs. Agarose in Medium Supplemented with IGF This experiment was conducted to determine the overall effect that a combination of medium with an effective concentration of IGF would have on would healing relative to a combination of medium and the anabolic hormone insulin. The results of this experiment evidenced that wound healing with medium plus insulin was substantially better through day 9 than was wound healing with medium plus IGF (See FIG. 12).

Example 15

Figure 13:
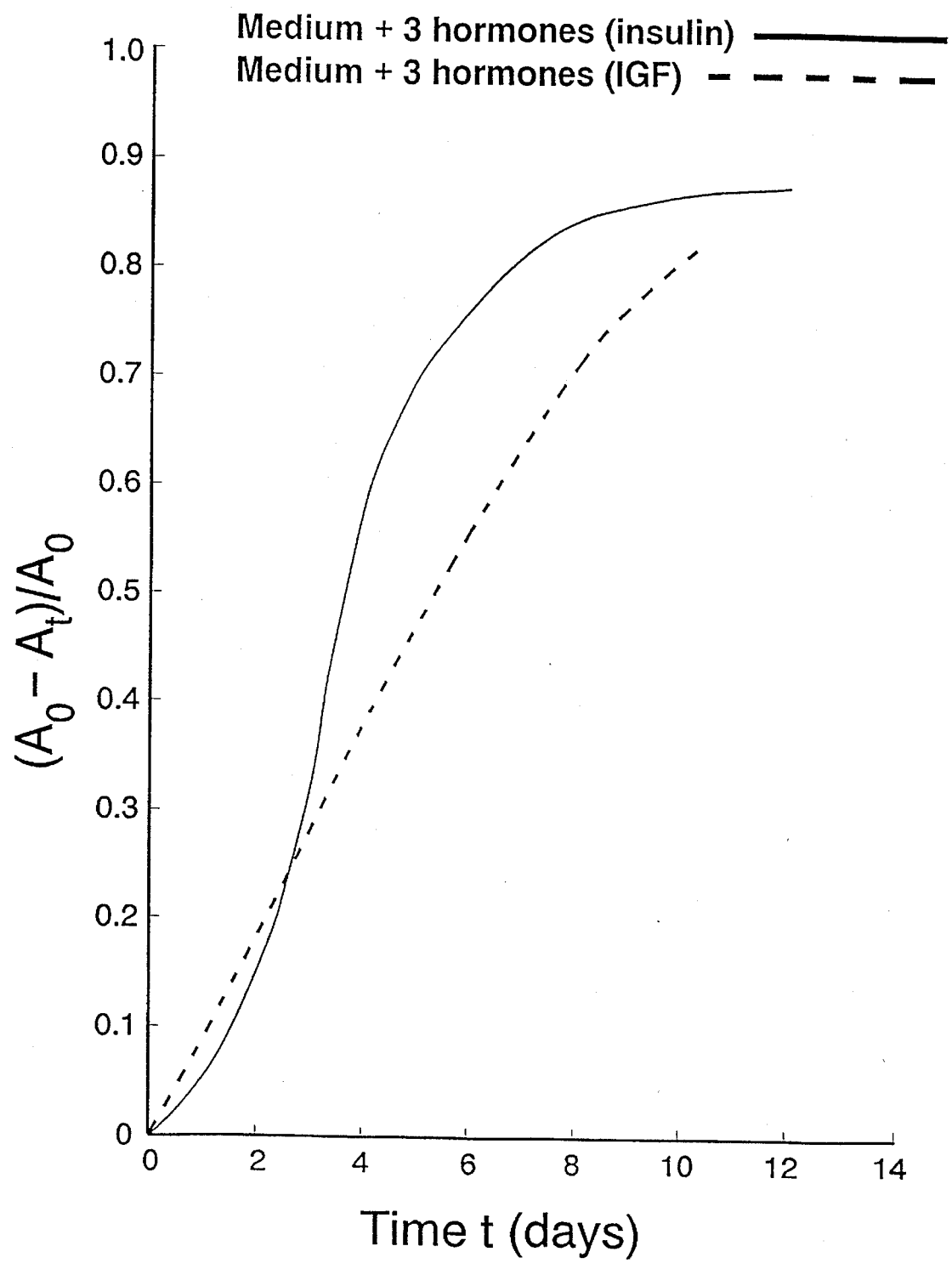

Agarose in Medium Supplemented with Insulin, Triiodothyronine/Thyroxine and Growth Hormone vs. Agarose in Medium Supplemented with IGF at 8 ng/ml, Triiodothyronine/Thyroxine and Growth Hormone This experiment was conducted to determine the overall effect that the substitution of IGF for insulin in a composition containing a mixture of the other two anabolic hormones would have on the wound healing effect. The results of this experiment evidenced that wound healing with medium plus insulin in the composition containing the other two hormones was substantially better than was wound healing with medium which included IGF, growth hormone and triiodothyronine/thyroxine (See FIG. 13).

Example 16

Figure 14:
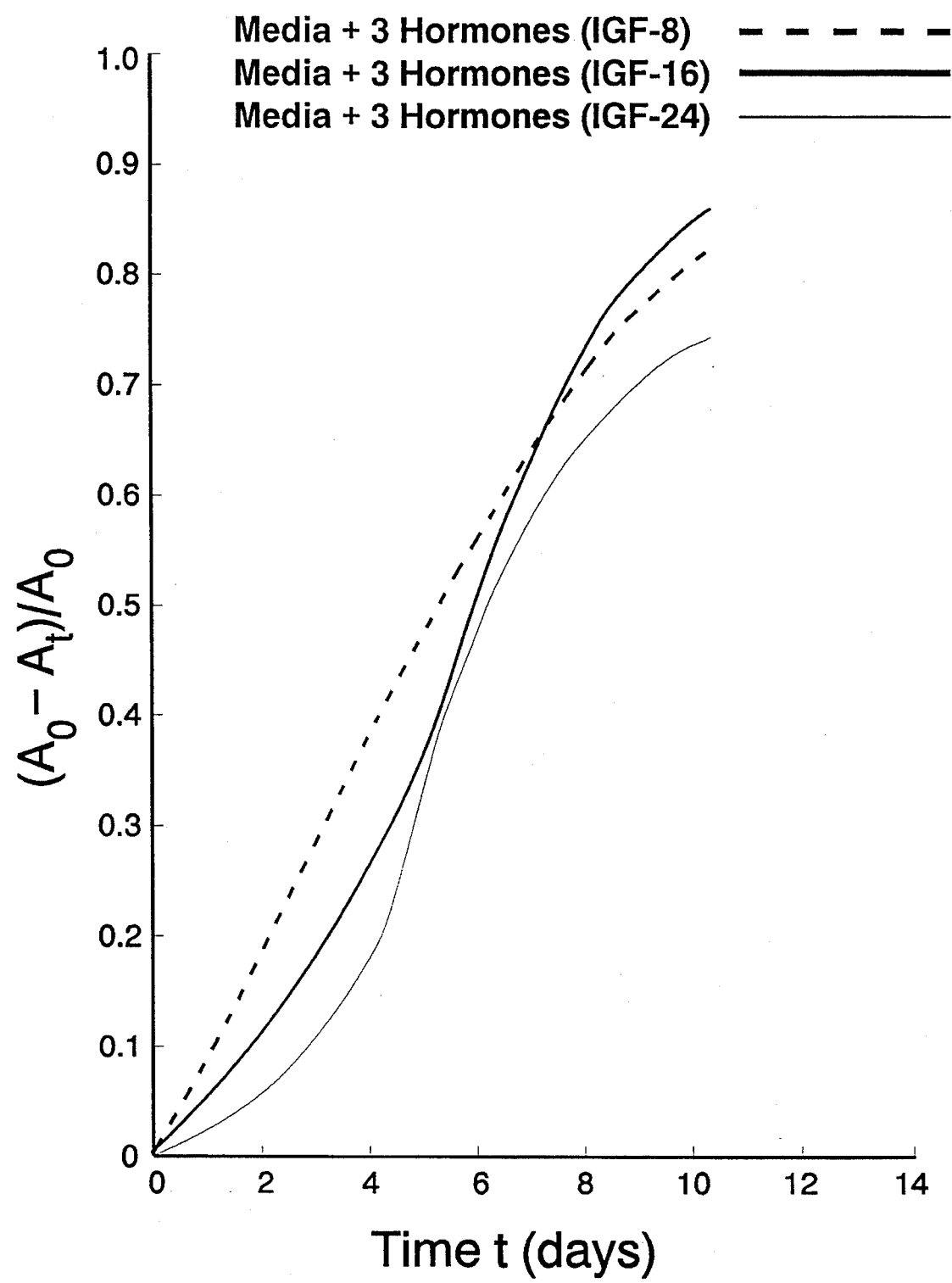

Agarose in Medium Supplemented with Triiodothyronine/Thyroxine, Growth Hormone and IGF at Concentrations of 8 ng/ml, 16 ng/ml and 24 ng/ml This experiment was conducted to determine the optimum concentration of IGF in a composition containing a mixture of IGF, growth hormone and the other two anabolic hormones. The results of this experiment evidenced that wound healing with IGF was maximal when IGF was included at a concentration of about 16 ng/ml. (See FIG. 14).

Example 17

Figure 15:
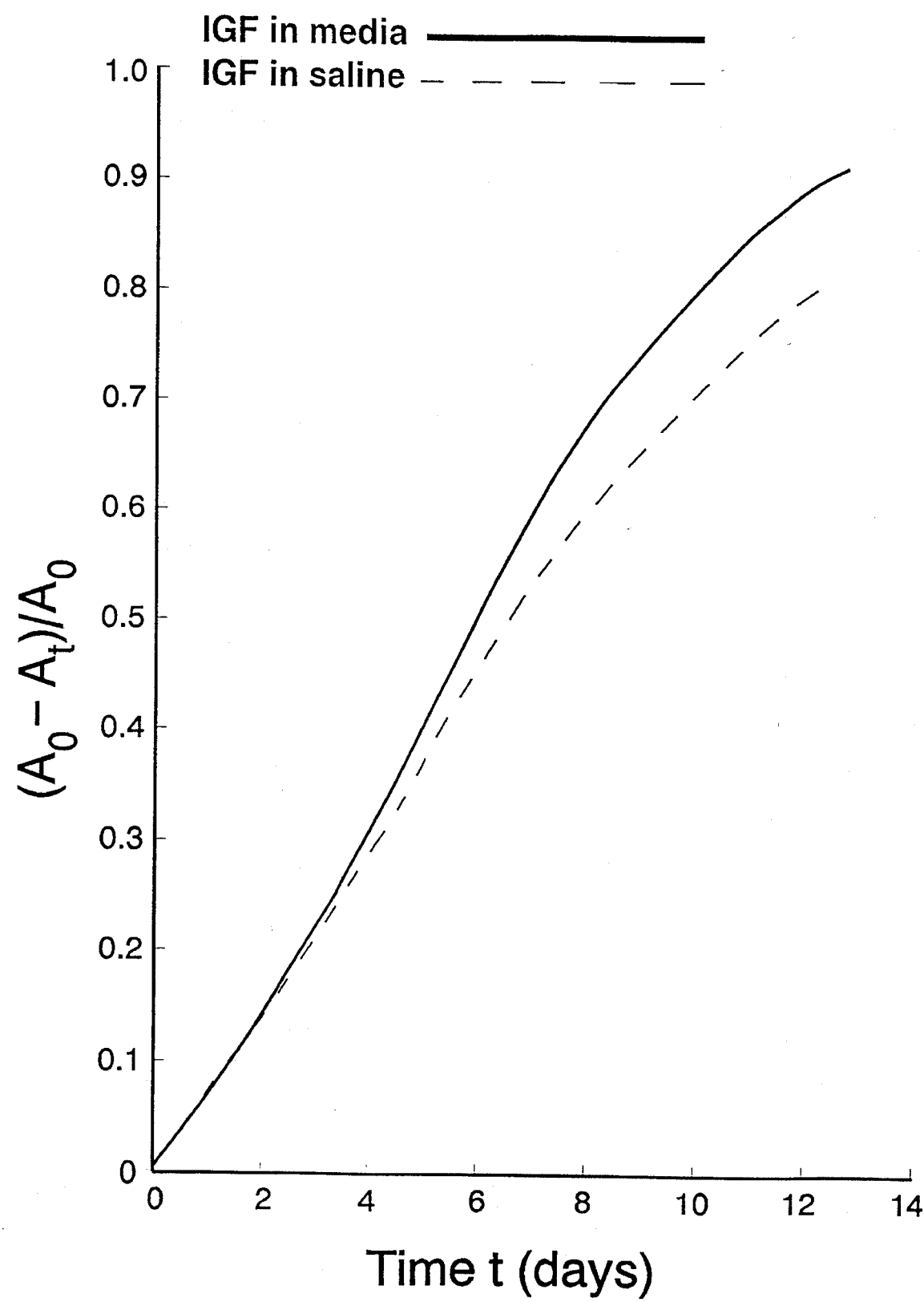

Agarose in Medium Supplemented with IGF at 8 ng/ml vs. Agarose in Saline Supplemented with IGF at 8 ng/ml This experiment was conducted to determine whether medium substantially affected the wound healing activity of IGF. The results of the experiments evidenced that IGF plus medium was substantially better at enhancing wound healing than was IGF in saline, however, this effect was seen later in the wound healing cycle. (See FIG. 15).

Conclusions

The following conclusions can be drawn from the results of the experiments presented herein:

Drug Delivery System

Using the formulations employed, use of Agarose improves wound closure rate as compared to gelatin. In particular, closure of wounds treated with saline in gelatin is about 33% slower than the closure of wounds treated with saline in Agarose.

Controls—Scarlet Red and Saline

The use of Scarlet Red dressing as positive control and saline as negative control yielded similar and slower closure when compared to media+hormone treatment.

Media and Hormone

The presence of at least one non-steroidal anabolic hormone and more preferably, a combination of three anabolic hormones in the presence of medium produces significant wound-healing benefit (wound closure rate is significantly higher). A combination of at least two anabolic hormones and medium also exhibited enhanced wound healing results (insulin and triiodothyronine/thyroxine or growth hormone and triiodothyronine/thyroxine). It is noted that a combination of insulin and growth hormone in animal test models did not evidence an enhancement in wound healing, although clinical human trials did indicate a benefit of the two hormones. Treatment with Gel media (in Agarose) devoid of hormonal supplement was slower than media plus hormone gel (three anabolic hormones) and was similar to the rate of closure found with treatment of Agarose in saline.

The presence of one anabolic hormone in media (insulin or triiodothyronine/thyroxine) evidenced significant wound healing activity vs. the same hormone in saline. Triiodothyronine and thyroxine exhibit similar activity at different levels (thyroxine has same effect as triiodothyronine at a concentration level about 3–5 times that of triiodothyronine). A combination of hormones showed similar (i.e., enhanced) results. The three hormones together in media was clearly the best combination.

The presence of IGF in media substantially enhanced wound healing relative to IGF in saline. However, the effectiveness of IGF in media was substantially less in all cases when compared to insulin. Any effect of IGF or PDGF on wound healing would most likely be exhibited, as it was here, late in the wound healing cycle. Thus, the inclusion of growth factors and in particular, IGF and PDGF, provides a possible enhancement of wound healing activity, either alone or in combination with at least one, more preferably two and most preferably three anabolic hormones.

Non-Quantifiable observations

The use of media containing hormone in agarose produces a scar which has a soft texture and a smooth surface (an unexpected result). It produces a more aesthetic and natural looking surface area as compared to scarlet red or saline. In most instances, no bulging nor any indentation occurred and the level of the scar tissue is continuous with the conformation of the surrounding non-wounded skin. The texture of the scar is also similar to that of surrounding non-wound tissue and discoloration eventually resolves.

The focus of our interest primarily was the rate of wound closure and our results using the animal model point to the efficacy of media supplemented with cellular growth stimulating compounds (preferably, non-steroidal anabolic hormones) according to the present invention, regardless of whether the rate of wound closure was due to wound contraction or epitheliazation or to a combination. With these two mechanisms taken into account, the exponential decrease in Wound area was nevertheless, significantly faster using media supplemented with hormones. The various controls used in this study illustrate that, both media alone and hormones alone, individually or together did not achieve the closure rates for the wounds treated with both. Furthermore, negative (scarlet red) and positive (saline) controls yielded similar and slower rates of closure.

Since trace quantities of growth factors constitute part of the wound exudate (Freshney, R. I. Culture of animal Cells. Alan R. Liss, Inc., N.Y., 1988, 2nd Edition, pp239–241 and Hayward and Robson, Animal Models of Wound Contraction In: *Clinical and Experimental Approaches to Dermal and Epidermal Repair; Normal and Clinical Wounds*, pp.301–312, 1991, Wiley-Liss, Inc.), none were added to the formulation of the gel media. While not being limited by way of theory, it is our hypothesis that the application of the gel media into the wound space created a complex, biologically active substrate which may act with the autologous growth factors which, in turn, reinforce the biological activity of the gel. The gel media combines the properties and characteristics of a biologically active material which, in addition, contains all the nutritional requirements for cellular proliferation. Our results regarding the gel's efficacy appear to agree with earlier findings showing early wound exudate to induce cellular proliferation (Mulder, G. D., If wounds could talk. *Clinical and Experimental Approaches to Dermal and Epidermal Repair; Normal and Chronic Wounds*, pp.55–66, 1991, Wiley-Liss, Inc.

The animal model presented herein imposes certain limitations: wounds are clean, surgically made and uncomplicated by contamination. This point is important since the gel media provides a growth substrate for bacteria. It is believed that, in contaminated wounds., a bacteriogram followed by or concomitant with specific antibiotic or disinfectant treatment in combination with the gel media treatment may be indicated.

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

I claim:

1. A method for treating a skin wound comprising applying to said wound a formulation comprising an effective amount of a mixture of non-steroidal anabolic hormones including insulin at a wound healing effective concentration within the range of about 500 ng/ml to about 100 ug/ml, growth hormone at a concentration of about 0.5 ng/ml to about 20 ng/ml and triiodothyronine or thyroxine at a concentration effective to enhance the healing of said wound in MCDB 153 nutrient medium, said formulation also including an amount of agarose, gelatin, collagen or a hydrophilic cellulose polymer effective to produce a gel for delivery to said wound.

2. A wound-treatment gel formulation comprising amounts of at least two non-steroidal anabolic hormones selected from the group consisting of insulin, growth hormone, triiodothyronine and thyroxine effective to enhance the healing of a skin wound in animals in combination with a cellular nutrient medium comprising essential amino acids, non-essential amino acids, a mixture of vitamins comprising amounts of folate, niacinamide, pantothenate, pyridoxine, riboflavin and thiamin, a mixture of inorganic ions comprising calcium, sodium, potassium, magnesium and chloride and glucose in amounts effective to enhance the healing of said wound in combination with said anabolic hormones, said formulation also including water and at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in amounts effective to form a gel for application of said formulation to said wound.

3. The formulation according to claim 2 wherein said cellular nutrient media is serum-free.

4. The formulation according to claim 3 wherein said polymer is gelatin, agarose, collagen or a hydrophilic cellulose polymer.

5. The formulation according to claim 2 further including an effective amount of a cellular growth factor or transforming factor selected from the group consisting of epithelial growth factor, transforming growth factor, platelet derived growth factor, insulin-like growth factor and mixtures thereof.

6. The formulation according to claim 3 including growth hormone at a concentration of about 0.5 ng/ml to about 50 ng/ml.

7. The formulation according to claim 3 wherein said anabolic hormone is insulin included at a concentration within the range of about 5 ng/ml to about 100 ug/ml.

8. The formulation according to claim 3 wherein said anabolic hormone is insulin included at a concentration of about 500 ng/ml to about 5 ug/ml.

9. The formulation according to claim 3 further including triiodothyronine or thyroxine at a concentration within the range of about 0.5 ng/ml to about 20 ng/ml.

10. The formulation according to claim 2 wherein said nutrient medium is a serum free nutrient medium selected from the group consisting of F10, F12, RPMI 1640, serum-free Dulbecco's Modified Eagle Medium, McCoy's 5A Medium, MCDB 153, Medium M199 including Earle's salt base and Minimum Essential Medium Eagle including non-essential amino acids and mixtures thereof.

11. The formulation according to claim 3 wherein said nutrient medium is MCDB 153.

12. The formulation according to claim 3 further including an effective amount of an antimicrobial agent.

13. The formulation according to claim 12 wherein said antimicrobial agent is an antibiotic.

14. The formulation according to claim 13 wherein said antibiotic is a cephalosporin or tetracycline.

15. A wound-treatment gel formulation comprising a mixture of non-steroidal anabolic hormones selected from at least two of the group consisting of insulin, triiodothyronine and thyroxine in an amount effective to enhance the healing of skin wounds in animals in combination with a cellular nutrient medium comprising essential amino acids, non-essential amino acids, a mixture of vitamins comprising amounts of folate, niacinamide, pantothenate, pyridoxine, riboflavin and thiamin, a mixture of inorganic ions comprising calcium, sodium, potassium, magnesium and chloride and glucose in amounts effective to enhance the healing of said wounds in combination with said anabolic hormones, said formulation also including water and at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in amounts within a range of about 1% to about 20% by weight of said formulation effective to form a gel for application of said formulation to a skin wound.

16. The formulation according to claim 15 further including growth hormone at a concentration of about 0.5 ng/ml to about 50 ng/ml.

17. The formulation according to claim 15 wherein said mixture of anabolic hormones includes insulin at a concentration within the range of about 500 ng/ml to about 100 ug/ml.

18. The formulation according to claim 16 wherein said mixture of anabolic hormones includes insulin at a concentration of about 500 ng/ml to about 100 ug/ml.

19. The formulation according to claim 15 wherein said mixture of anabolic hormones includes thyroxine.

20. The formulation according to claim 15 wherein said polymer is agarose or gelatin.

21. A gel formulation for topical application to the skin of animals comprising a mixture of insulin and triiodothyronine, said insulin being included in said formulation at a wound healing effective concentration within the range of about 5 ng/ml to about 100 ug/ml and said triiodothyronine being included in said formulation at a wound healing effective concentration within the range of about 0.5 ng/ml to about 50 ng/ml in combination with a serum free cellular nutrient medium selected from the group consisting of F10, F12, Basal Medium Eagle including Earle's salt base, Dulbecco's Modified Eagle Medium, McCoy's 5A Medium, MCDB 153, Medium M199 including Earle's salt base, Medium M199 including Hank's salt base, Minimum Essential Medium Eagle including Earle's salt base, Minimum Essential Medium Eagle including Hank's salt base, Minimum Essential Medium Eagle with non-essential amino acids and mixtures thereof in an amount effective to enhance the healing of skin wounds in combination with said insulin and said triiodothyronine, said formulation also including water and at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in amounts within a range of about 1% to about 20% by weight of said formulation effective to form a gel for topical application of said formulation to said skin.

22. The formulation according to claim 21 further including growth hormone at a concentration of about 0.5 ng/ml to about 50 ng/ml.

23. A method for treating skin wounds in animals comprising applying to said wound a formulation comprising an amount of a non-steroidal anabolic hormone selected from the group consisting of insulin, triiodothyronine, thyroxine and mixtures thereof effective to enhance the healing of said wounds in combination with a nutrient medium comprising essential amino acids, non-essential amino acids, a mixture of vitamins comprising amounts of folate, niacinamide, pantothenate, pyridoxine, riboflavin and thiamin, a mixture of inorganic ions comprising calcium, sodium, potassium, magnesium and chloride and glucose in amounts effective to enhance the healing of said wounds in combination with said anabolic hormone.

24. The method according to claim 23 wherein said formulation further includes growth hormone at a concentration of about 0.5 ng/ml to about 50 ng/ml.

25. The method according to claim 24 wherein each of said anabolic hormones other than insulin is included at a concentration ranging from about 0.5 ng/ml to about 20 ng/ml.

26. A wound-treatment gel formulation comprising a mixture of insulin, growth hormone and at least one additional anabolic hormone selected from the group consisting of triiodothyronine, thyroxine and mixtures thereof, said insulin, growth hormone and additional anabolic hormone being included in said formulation in an amount effective to enhance the healing of skin wounds in animals in combination with a cellular nutrient medium comprising essential amino acids, non-essential amino acids, a mixture of vitamins comprising amounts of folate, niacinamide, pantothenate, pyridoxine, riboflavin and thiamin, a mixture of inorganic ions comprising calcium, sodium, potassium, magnesium and chloride and glucose in amounts effective to enhance the healing of said wounds in combination with said insulin, growth hormone and additional anabolic hormone, said formulation also including water and at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in an amount effective to form a gel for application of said formulation to a skin wound.

27. The formulation according to claim 26 wherein said polymer is selected from the group consisting of agarose, gelatin, collagen and a hydrophilic cellulose polymer.

28. A method for treating skin wounds in animals comprising applying to said wound a formulation comprising a wound-healing effective amount of a non-steroidal anabolic hormone selected from the group consisting of insulin, triiodothyronine, thyroxine and mixtures thereof in combination with a serum free nutrient medium selected from the group consisting of F10, F12, Basal Medium Eagle including Earle's salt base, Dulbecco's Modified Eagle Medium, McCoy's 5A Medium, MCDB 153, Medium M199 including Earle's salt base, Medium M199 including Hank's salt base, Minimum Essential Medium Eagle including Earle's salt base, Minimum Essential Medium Eagle including Hank's salt base, Minimum Essential Medium Eagle with non-essential amino acids and mixtures thereof in amounts effective to enhance the healing of said wounds in combination with said anabolic hormone.

29. The method according to claim 28 further including a wound healing effective amount of growth hormone.

30. The method according to claim 29 wherein said growth hormone is included within the range of about 0.5 ng/ml to about 50 ng/ml.

31. The method according to claim 28 wherein said hormone is insulin included at a concentration within the range of about 500 ng/ml to about 100 ug/ml.

32. The method according to claim 29 wherein said hormone is insulin included at a concentration within the range of about 500 ng/ml to about 100 ug/ml.

33. The method according to claim 31 wherein said composition includes triiodothyronine or thyroxine at a wound healing effective concentration.

34. The method according to claim 32 including thyroxine at a wound healing effective concentration.

35. A gel formulation for topical application to the skin of animals comprising a mixture of insulin and triiodothyronine or thyroxine, said insulin being included in said formulation at a wound healing effective concentration within the range of about 500 ng/ml to about 100 ug/ml and said triiodothyronine or thyroxine being included in said formulation at a wound healing effective concentration in combination with a serum free cellular nutrient medium selected from the group consisting of F10, F12, Basal Medium Eagle including Earle's salt base, Dulbecco's Modified Eagle Medium, MCDB 153, McCoy's 5A Medium, Medium M199 including Earle's salt base, Medium M199 including Hank's salt base, Minimum Essential Medium Eagle including Earle's salt base, Minimum Essential Medium Eagle including Hank's salt base, Minimum Essential Medium Eagle with non-essential amino acids and mixtures thereof in an amount effective to enhance the healing of skin wounds in combination with said insulin and said triiodothyronine or thyroxine, said formulation also including water and at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in amounts within a range of about 1% to about 20% by weight of said formulation effective to form a gel for topical application of said formulation to said skin.

36. The formulation according to claim 35 further including growth hormone at a concentration of about 0.5 ng/ml to about 50 ng/ml.

37. A wound-treatment formulation comprising a mixture of insulin, growth hormone and at least one additional anabolic hormone selected from the group consisting of triiodothyronine, thyroxine and mixtures thereof, said insulin, growth hormone and additional anabolic hormone being included in said formulation in an amount effective to enhance the healing of skin wounds in animals in combination with a cellular nutrient medium comprising essential amino acids, non-essential amino acids, a mixture of vitamins comprising amounts of folate, niacinamide, pantothenate, pyridoxine, riboflavin and thiamin, a mixture of inorganic ions comprising calcium, sodium, potassium, magnesium and chloride and glucose in amounts effective to enhance the healing of said wounds in combination with said insulin, growth hormone and additional anabolic hormone, said formulation also including at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in an amount effective to form a gel in combination with water for application of said formulation to a skin wound.

38. A wound-treatment formulation comprising a mixture of insulin, growth hormone and at least one additional anabolic hormone selected from the group consisting of triiodothyronine, thyroxine and mixtures thereof, said insulin, growth hormone and additional anabolic hormone being included in said formulation in an amount effective to enhance the healing of skin wounds in animals in combination with a cellular nutrient medium selected from the group consisting of F10, F12, Basal Medium Eagle including Earle's salt base, Dulbecco's Modified Eagle Medium, McCoy's 5A Medium, MCDB 153, Medium M199 including Earle's salt base, Medium M199 including Hank's salt base, Minimum Essential Medium Eagle including Earle's salt base, Minimum Essential Medium Eagle including Hank's salt base, Minimum Essential Medium Eagle with non-essential amino acids and mixtures thereof, said formulation also including at least one polymer selected from the group consisting of polyhydroxyethylmethacrylate, polyvinylpyrrolidone, polyethylene glycol, gelatin, sepharose, agarose, collagen, cellulose, dextran, polyethyleneoxide, dextran-polyethylene, polyacrylamide, amylose, a hydrophilic cellulose polymer and mixtures thereof in an amount effective to form a gel in combination with water for application of said formulation to a skin wound.

* * * * *